United States Patent
Abal et al.

(10) Patent No.: US 12,125,573 B2
(45) Date of Patent: Oct. 22, 2024

(54) WASTING STATION FOR MEDICATIONS

(71) Applicant: CareFusion 303, Inc., San Diego, CA (US)

(72) Inventors: Daniel Abal, San Diego, CA (US); Brendan John Burgess, Poway, CA (US); Ramkumar Subramanian, San Diego, CA (US); Mustafa Yusufi, Escondido, CA (US); Clarence Wu, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 554 days.

(21) Appl. No.: 17/317,507

(22) Filed: May 11, 2021

(65) Prior Publication Data

US 2021/0358257 A1   Nov. 18, 2021

Related U.S. Application Data

(60) Provisional application No. 63/024,983, filed on May 14, 2020.

(51) Int. Cl.
*G16H 20/13* (2018.01)
*G06Q 10/30* (2023.01)
*G16H 40/20* (2018.01)

(52) U.S. Cl.
CPC ............ *G16H 20/13* (2018.01); *G06Q 10/30* (2013.01); *G16H 40/20* (2018.01)

(58) Field of Classification Search
None
See application file for complete search history.

(56) References Cited

U.S. PATENT DOCUMENTS

| 4,551,133 A | 11/1985 | Zegers de Beyl et al. |
| 5,945,651 A | 8/1999 | Chorosinski et al. |

(Continued)

FOREIGN PATENT DOCUMENTS

| AU | 2017 279 693 A1 | 1/2018 |
| AU | 2018335288 B2 | 8/2023 |

(Continued)

OTHER PUBLICATIONS

Benjamin, X.C. et al. (2012). "Visual identification of medicine boxes using features matching." *IEEE International Conference on Virtual Environments Human-Computer Interfaces and Measurement Systems (VECIMS) Proceedings*, 43-47. Doi: 10.1109/VECIMS.2012.6273190.

(Continued)

*Primary Examiner* — Jan P Mincarelli
(74) *Attorney, Agent, or Firm* — Mintz Levin Cohn Ferris Glovsky and Popeo, P.C.

(57) ABSTRACT

A wasting station for receiving a wasted medication from a medication dispenser is provided. The wasting station includes a base and a locking mechanism. The base includes a weight sensor to measure a weight of a waste container supported by the base. The wasting station can determine, based on the measured weight, a volume of the wasted medication positioned within the waste container. The locking mechanism includes a first end coupled to the base. The locking mechanism also includes a second end coupled to the waste container when the locking mechanism is in a first position and decoupled from the waste container when the (Continued)

locking mechanism moves from the first position to a second position, thereby allowing for removal of the waste container.

19 Claims, 16 Drawing Sheets

(56) References Cited

U.S. PATENT DOCUMENTS

| | | | |
|---|---|---|---|
| 5,961,036 A | 10/1999 | Michael et al. | |
| 5,991,731 A | 11/1999 | Colon et al. | |
| 6,650,964 B2 | 11/2003 | Spano, Jr. et al. | |
| 6,671,579 B2 | 12/2003 | Spano, Jr. et al. | |
| 6,842,736 B1 | 1/2005 | Brzozowski | |
| 6,868,344 B1 | 3/2005 | Nelson | |
| 7,119,689 B2 | 10/2006 | Mallett et al. | |
| 7,184,897 B2 | 2/2007 | Nelson | |
| 7,275,645 B2 | 10/2007 | Mallett et al. | |
| 7,303,081 B2 | 12/2007 | Mallett et al. | |
| 7,311,207 B2 | 12/2007 | Mallett et al. | |
| 7,318,529 B2 | 1/2008 | Mallett et al. | |
| 7,562,025 B2 | 7/2009 | Mallett et al. | |
| 7,693,603 B2 | 4/2010 | Higham | |
| 8,147,479 B1 | 4/2012 | Wach et al. | |
| 8,195,328 B2 | 6/2012 | Mallett et al. | |
| 8,280,550 B2 | 10/2012 | Levy et al. | |
| 8,319,669 B2 | 11/2012 | Weller | |
| 8,357,114 B2 | 1/2013 | Poutiatine et al. | |
| 8,595,021 B2 | 11/2013 | Mallett et al. | |
| 8,606,596 B1 | 12/2013 | Bochenko et al. | |
| 8,725,532 B1 | 5/2014 | Ringold | |
| 8,738,177 B2 | 5/2014 | van Ooyen et al. | |
| 8,768,724 B2 | 7/2014 | Whiddon et al. | |
| 8,905,964 B2 | 12/2014 | Poutiatine et al. | |
| 9,158,892 B2 | 10/2015 | Levy et al. | |
| 9,202,052 B1 | 12/2015 | Fang et al. | |
| 9,227,025 B2 | 1/2016 | Butterfield et al. | |
| 9,354,178 B2 | 5/2016 | Lee | |
| 9,427,520 B2 | 8/2016 | Batch et al. | |
| 9,456,958 B2 | 10/2016 | Reddy et al. | |
| 9,523,635 B2 | 12/2016 | Tilden | |
| 9,636,273 B1 | 5/2017 | Harris | |
| 9,752,935 B2 | 9/2017 | Marquardt et al. | |
| 9,796,526 B2 | 10/2017 | Smith et al. | |
| 9,817,850 B2 | 11/2017 | Dubbels et al. | |
| 9,836,485 B2 | 12/2017 | Dubbels et al. | |
| 9,842,196 B2 | 12/2017 | Utech et al. | |
| 9,881,129 B1 | 1/2018 | Cave | |
| 9,958,324 B1 | 5/2018 | Marquardt et al. | |
| 10,032,344 B2 | 7/2018 | Nelson et al. | |
| 10,101,269 B2 | 10/2018 | Judge et al. | |
| 10,187,288 B2 | 1/2019 | Parker et al. | |
| 10,209,176 B2 | 2/2019 | Proskurowski et al. | |
| 10,241,038 B2 | 3/2019 | Nishimura et al. | |
| 10,249,153 B2 | 4/2019 | Nelson et al. | |
| 10,309,832 B2 | 6/2019 | Marquardt et al. | |
| 10,345,242 B2 | 7/2019 | Zhao et al. | |
| 10,832,207 B2 | 11/2020 | Vahlberg et al. | |
| 11,037,666 B1 | 6/2021 | Benoit et al. | |
| 11,116,892 B2 | 9/2021 | Brady et al. | |
| 11,147,914 B2 | 10/2021 | Estes | |
| 11,481,739 B1* | 10/2022 | McKinzie | G01G 19/52 |
| 2003/0158751 A1 | 8/2003 | Suresh et al. | |
| 2007/0260487 A1 | 11/2007 | Bartfeld et al. | |
| 2008/0059226 A1 | 3/2008 | Melker et al. | |
| 2008/0082360 A1 | 4/2008 | Bailey et al. | |
| 2008/0140715 A1 | 6/2008 | Hakos | |
| 2008/0243055 A1 | 10/2008 | Fathallah et al. | |
| 2008/0288430 A1 | 11/2008 | Friedlander et al. | |
| 2008/0306796 A1 | 12/2008 | Zimmerman et al. | |
| 2008/0319795 A1 | 12/2008 | Poteet et al. | |
| 2009/0083231 A1 | 3/2009 | Eberholst et al. | |
| 2009/0160646 A1 | 6/2009 | Mackenzie et al. | |
| 2010/0169063 A1 | 7/2010 | Yudkovitch et al. | |
| 2010/0213250 A1 | 8/2010 | Mallett et al. | |
| 2011/0016110 A1 | 1/2011 | Egi et al. | |
| 2011/0082440 A1 | 4/2011 | Kimmo et al. | |
| 2011/0161108 A1 | 6/2011 | Miller et al. | |
| 2012/0226447 A1 | 9/2012 | Nelson et al. | |
| 2012/0265336 A1 | 10/2012 | Mallett et al. | |
| 2012/0305132 A1* | 12/2012 | Maness | B09B 3/70 141/69 |
| 2012/0325330 A1 | 12/2012 | Prince et al. | |
| 2013/0002429 A1 | 1/2013 | Johnson | |
| 2013/0018356 A1* | 1/2013 | Prince | G06Q 10/0833 604/506 |
| 2013/0070090 A1 | 3/2013 | Bufalini et al. | |
| 2013/0144254 A1 | 6/2013 | Amirouche et al. | |
| 2013/0158705 A1 | 6/2013 | Levy et al. | |
| 2013/0253291 A1 | 9/2013 | Dixon et al. | |
| 2013/0253700 A1 | 9/2013 | Carson et al. | |
| 2013/0262138 A1 | 10/2013 | Jaskela et al. | |
| 2013/0282392 A1 | 10/2013 | Wurm | |
| 2013/0325727 A1* | 12/2013 | MacDonell | A61B 50/10 705/308 |
| 2014/0074284 A1 | 3/2014 | Czaplewski et al. | |
| 2014/0081652 A1 | 3/2014 | Klindworth | |
| 2014/0149131 A1 | 5/2014 | Bear et al. | |
| 2014/0249776 A1 | 9/2014 | King et al. | |
| 2014/0277707 A1 | 9/2014 | Akdogan et al. | |
| 2014/0375324 A1 | 12/2014 | Matsiev et al. | |
| 2015/0038898 A1 | 2/2015 | Palmer et al. | |
| 2015/0061832 A1 | 3/2015 | Pavlovic et al. | |
| 2015/0081324 A1 | 3/2015 | Adjaoute | |
| 2015/0109437 A1 | 4/2015 | Yang et al. | |
| 2015/0161558 A1 | 6/2015 | Gitchell et al. | |
| 2015/0221086 A1 | 8/2015 | Bertram | |
| 2015/0272825 A1 | 10/2015 | Lim et al. | |
| 2015/0286783 A1 | 10/2015 | Kumar et al. | |
| 2015/0294079 A1 | 10/2015 | Bergougnan | |
| 2015/0323369 A1 | 11/2015 | Marquardt | |
| 2015/0339456 A1 | 11/2015 | Sprintz | |
| 2015/0362350 A1 | 12/2015 | Miller et al. | |
| 2016/0034274 A1 | 2/2016 | Diao et al. | |
| 2016/0062371 A1 | 3/2016 | Davidian et al. | |
| 2016/0117478 A1 | 4/2016 | Hanina et al. | |
| 2016/0132649 A1 | 5/2016 | Gitchell et al. | |
| 2016/0161705 A1 | 6/2016 | Marquardt et al. | |
| 2016/0166766 A1 | 6/2016 | Schuster et al. | |
| 2016/0259904 A1 | 9/2016 | Wilson | |
| 2016/0259911 A1 | 9/2016 | Koester | |
| 2016/0283691 A1 | 9/2016 | Ali | |
| 2017/0017760 A1 | 1/2017 | Freese et al. | |
| 2017/0032102 A1 | 2/2017 | Skoda | |
| 2017/0076065 A1 | 3/2017 | Darr et al. | |
| 2017/0083681 A1 | 3/2017 | Sprintz et al. | |
| 2017/0103203 A1 | 4/2017 | Sharma et al. | |
| 2017/0108480 A1 | 4/2017 | Clark et al. | |
| 2017/0109480 A1 | 4/2017 | Vahlberg | |
| 2017/0109497 A1 | 4/2017 | Tribble et al. | |
| 2017/0120035 A1 | 5/2017 | Butterfield et al. | |
| 2017/0199983 A1* | 7/2017 | Cano | A61J 7/02 |
| 2018/0028408 A1 | 2/2018 | Li et al. | |
| 2018/0039736 A1 | 2/2018 | Williams | |
| 2018/0046651 A1 | 2/2018 | Dubbels et al. | |
| 2018/0157803 A1 | 6/2018 | Mirov | |
| 2018/0165417 A1 | 6/2018 | Hall et al. | |
| 2018/0192942 A1 | 7/2018 | Clark et al. | |
| 2018/0203978 A1 | 7/2018 | Basu et al. | |
| 2018/0231415 A1 | 8/2018 | Marquardt et al. | |
| 2018/0247703 A1 | 8/2018 | D'Amato | |
| 2018/0259446 A1 | 9/2018 | Coffey et al. | |
| 2018/0299375 A1 | 10/2018 | Young et al. | |
| 2018/0330824 A1 | 11/2018 | Athey et al. | |
| 2018/0365385 A1 | 12/2018 | Cooney et al. | |
| 2018/0365386 A1 | 12/2018 | Vanderveen | |
| 2019/0088354 A1 | 3/2019 | Yanowitz et al. | |
| 2019/0117883 A1 | 4/2019 | Abrams et al. | |
| 2019/0124118 A1 | 4/2019 | Swafford | |
| 2019/0139638 A1 | 5/2019 | Keefe et al. | |
| 2019/0180862 A1 | 6/2019 | Wisser et al. | |
| 2019/0244699 A1 | 8/2019 | Loebig et al. | |
| 2019/0247703 A1 | 8/2019 | Welde et al. | |
| 2019/0341142 A1 | 11/2019 | Nag et al. | |

(56) References Cited

U.S. PATENT DOCUMENTS

| | | |
|---|---|---|
| 2019/0355461 A1 | 11/2019 | Kumar et al. |
| 2020/0085686 A1 | 3/2020 | Aliakbarian et al. |
| 2020/0098474 A1 | 3/2020 | Vanderveen |
| 2020/0219611 A1 | 7/2020 | Nag et al. |
| 2020/0222627 A1 | 7/2020 | Guerra et al. |
| 2020/0230316 A1 | 7/2020 | Guerra et al. |
| 2020/0312442 A1* | 10/2020 | Hairr ............... G16H 40/20 |
| 2020/0402632 A1 | 12/2020 | van Schelven et al. |
| 2021/0005324 A1 | 1/2021 | Bostic et al. |
| 2021/0027259 A1 | 1/2021 | Burgess et al. |
| 2021/0133201 A1 | 5/2021 | Tribble et al. |
| 2021/0249121 A1 | 8/2021 | Burgess et al. |
| 2021/0308385 A1 | 10/2021 | Nisha et al. |
| 2022/0062964 A1* | 3/2022 | VanDerWoude ....... A61B 50/39 |
| 2022/0093239 A1 | 3/2022 | Nag et al. |

FOREIGN PATENT DOCUMENTS

| | | |
|---|---|---|
| CA | 2 636 115 C | 6/2014 |
| CA | 2 848 274 C | 9/2016 |
| EP | 1 973 593 B1 | 4/2013 |
| EP | 1 593 076 B1 | 10/2019 |
| JP | 2016-517077 A | 6/2016 |
| KR | 10-2014-0129141 A | 11/2014 |
| WO | WO-2006/034367 A2 | 3/2006 |
| WO | WO-2010/058796 A1 | 5/2010 |
| WO | WO-2011/014517 A1 | 2/2011 |
| WO | WO-2011/039676 A2 | 4/2011 |
| WO | WO-2012121991 A1 * | 9/2012 ............ A61M 5/168 |
| WO | WO-2014/055925 A1 | 4/2014 |
| WO | WO-2015/187682 A1 | 12/2015 |
| WO | WO-2019/028004 A1 | 2/2019 |
| WO | WO-2019/031331 A1 | 2/2019 |
| WO | WO-2020/206154 A1 | 10/2020 |

OTHER PUBLICATIONS

Cakaloglu, T. (Nov. 1, 2017). "Medi-Deep: Deep control in a medication usage." *2017 IEEE International Conference of Bioinfomratice and Biomedicine (BIBM)*, 899-904. Doi: 10.1109/BIBM.2017.8217776.

Neuman, M.R. et al. (May 13, 2012). "Advances in Medical Devices and Medical Electronics," in Proceedings of the IEEE, vol. 100, No. Special Centennial Issue, pp. 1537-1550,doi: 10.1109/JPROC.2012.2190684.

Qui et al. (2016). "A survey of machine learning for big data processing." *EURASIP Journal on Advances in Signal Processing*, Article No. 67, 16 pages.

Shishvan, O. Rajabi et al. (2018). "Machine Intelligence in Healthcare and Medical Cyber Physical Systems: A Survey." *IEEE Access.* vol. 6, 46419-46494. doi: 10.1109/ACCESS.2018.2866049.

Uniyal, D. et al. (Nov. 7, 2014). "Pervasive Healthcare—A Comprehensive Survey of Tools and Techniques," arXiv:1411.1821v1, 48 pages.

Yang, J., McAuley, J.J., & Leskovec, J. (2013). "Community Detection in Networks with Node Attributes." 2013 IEEE 13th International Conference on Data Mining, 1151-1156.

Yaniv, Z. et al. (Oct. 1, 2016). "The National Library of Medicine Pill Image Recognition Challenge: An Initial Report." *Oct. 2016 IEEE Applied Imagery Pattern Recognition Workshop, (AIPR)*, 1-9. Doi: 10.1109/AIPR.2016.8010584.

Zhan, A. et al. (Jan. 5, 2016). "High Frequency Remote Monitoring of Parkinson's Disease via Smartphone: Platform Overview and Medication Response Detection," Retrieved Apr. 29, 2021. 12 pages.

\* cited by examiner

WASTING STATION FOR MEDICATIONS

CROSS-REFERENCE TO RELATED APPLICATIONS

The present application claims priority to U.S. Provisional Application No. 63/024,983, filed on May 14, 2020, and entitled "Wasting Station for Medications," the entirety of which is incorporated by reference herein.

TECHNICAL FIELD

The subject matter described herein relates generally to secure disposal and/or wasting of medications.

BACKGROUND

Diversion may refer to the transfer of a controlled substance to a third party who is not legally (or otherwise) authorized to receive, possess, administer, and/or consume the controlled substance. High-value and/or controlled prescription medications, notably opioids, may be especially prone to diversion. For instance, prescription medications may be diverted while being loaded into and/or retrieved from a dispensing cabinet. Some prescription medications, such as morphine, hydromorphone, fentanyl, and/or the like, may be administered to a patient via a pump, for example, a patient-controlled analgesic (PCA) pump, that is capable of holding more doses of the prescription medication than is needed by the patient or administering partial doses for a patient. The extra or residual doses of prescription medication may be susceptible to being diverted by the clinicians. For example, some of the prescription medication may be removed before being loaded into the pump and/or administered to the patient. Alternatively and/or additionally, prescription medication that remains in the pump and/or that has not been administered to the patient may be held back instead of properly disposed of at a wasting site.

SUMMARY

Systems, methods, and articles of manufacture, including computer program products, are provided for securely and efficiently wasting medications and auditing the wasting of medications.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1A:
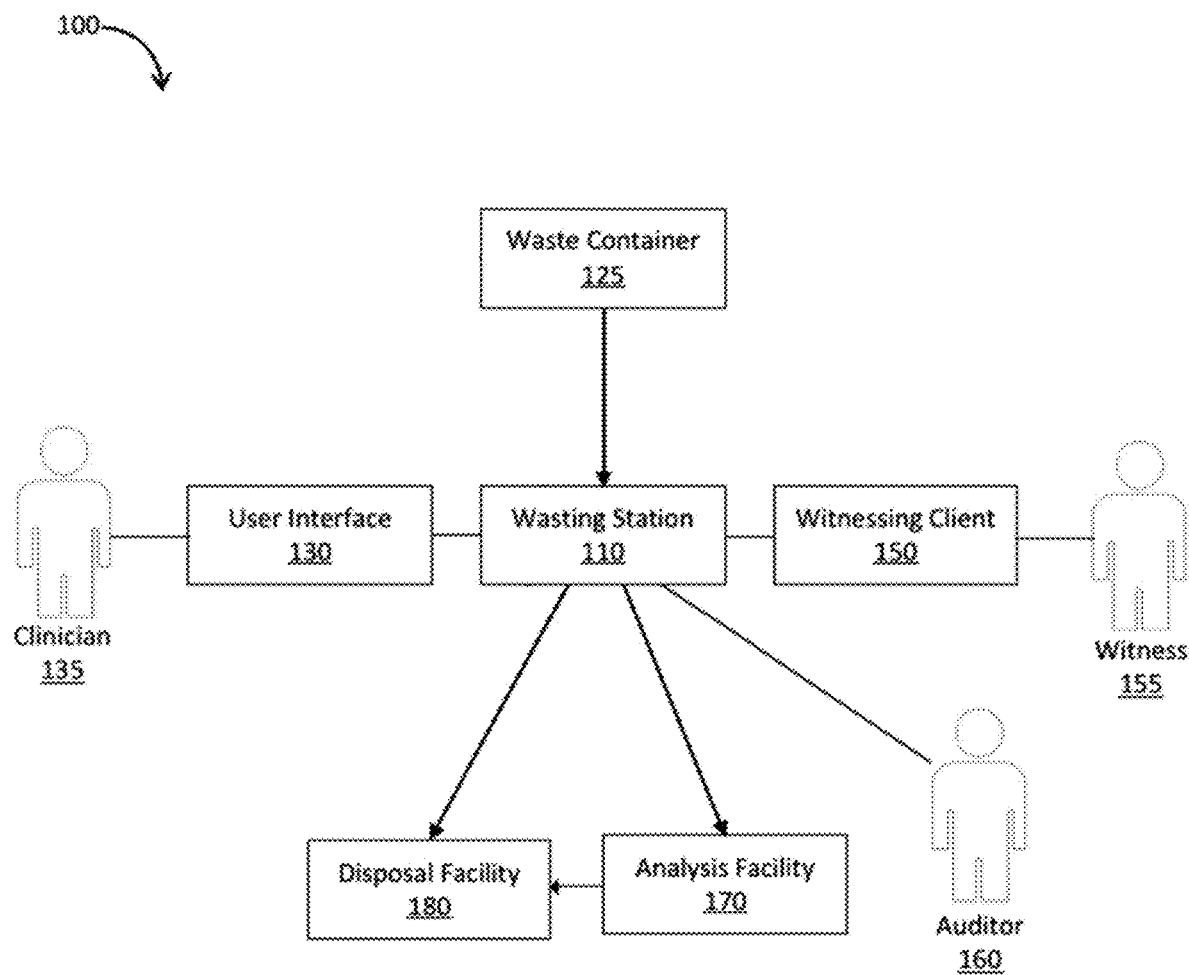
FIG. 1A and FIG. 1B are system diagrams depicting aspects of a wasting system, consistent with implementations of the current subject matter.

Diversion of a medication may occur at any point in time including, for example, during the shipping, receiving, stocking, dispensing, administering, or wasting of the medication. Prescription pain medication may be especially prone to diversion due to a lack of sufficient custodial oversight, for example, during the shipping, receiving, stocking, dispensing, administering, or wasting of the prescription pain medication. For example, dispensing cabinets at medical facilities may be accessible to multiple clinicians or other personnel or users. Moreover, different users may be responsible for different aspects of dispensing, administering, and/or wasting of the medication. Thus, even if diversion is detected, it may be difficult to determine when the diversion actually occurred and to further identify the person or persons responsible for the diversion.

To provide incentives to not engage in predatory or improper practices, such as the diversion of medication and/or improper wasting of medication, and to identify clinicians or other users who may be engaged in the predatory practices, a wasting system consistent with implementations of the current subject matter includes a wasting station. The wasting station includes features for securely receiving, storing, and identifying wasted medication for later analysis, such as during an audit. The wasting station may further include capabilities to analyze waste items. The wasting system may including one or more sensors and may provide for waste containers that include electronic tags, biomarkers, and/or reagents that may be used to analyze waste items.

The wasting system including the wasting station consistent with implementations of the current subject matter may be used to dispose of fluid medications, such as medication from a syringe, an intravenous bag or other types of fluid containers, and/or leftover solid medications, such as pills, patches, or other solids after a portion of the medication has been administered to a patient. For example, the wasting system may allow for multiple syringes to be emptied into a waste container in various sequences. The wasting system may accurately measure and/or track the dispensed weight and/or volume of the wasted medication that is deposited into and/or captured by a waste container. The wasting system may additionally and/or alternatively identify the wasted medication, such as when the medication is deposited into the waste container. The wasting system may additionally and/or alternatively secure the wasting station, such that only authorized users may access one or more components of the wasting station.

In some situations, a medication may be wasted at the wasting station. Generally, wasting stations do not provide for the ability to control access to the waste container. These wasting stations allow a clinician or other user easy access to the waste container after the medication is wasted, and do little to prevent or limit diversion of wasted medication. For example, wasting stations may not include sufficient preventative measures that reduce the likelihood that the waste containers will be removed by an unauthorized user, at an unauthorized time, and/or the like. The wasting system including the wasting station described herein includes one or more locking systems and/or authentication systems that helps to ensure that only an authorized user is granted access to the waste container to waste medication and/or remove the waste container.

Additionally and/or alternatively, wasting stations generally fail to provide accurate measurements of the amount of waste be wasted into a particular waste container and/or fail to verify the amount of waste that actually enters the waste container. For example, some wasting stations may only rely on a sensor, such as a flow sensor, to determine the amount of waste that has been deposited into a waste container. While such sensors may determine the amount of waste that passes the flow sensor, wasting stations using only these sensors to detect the amount of waste deposited to the waste container fail to accurately measure the amount of waste actually deposited into the waste container. Thus, such systems may allow clinicians or other users to more easily engage in "predatory" procedures when wasting, as these systems may have no way of verifying the actual amount of waste that has been wasted and deposited into the waste container. The wasting system including the wasting station described herein includes one or more sensors, such as a weight sensor, load sensor and/or load cell, and/or the like, that determines a weight of the medication wasted into the waste container to verify and/or otherwise calculate an accurate amount of waste that has been wasted into the waste container. This helps to prevent or limit diversion by verifying that the correct amount of medication has actually been deposited into the waste container. This also helps during a later audit, as the wasting system can track and/or compare the amount of medication that should have been deposited into the waste container and the amount of medication actually deposited into the waste container. The wasting system may additionally and/or alternatively track the user and the weight measurements for later analysis and/or audit, to help identify a clinician or other user engaging in diversion.

Additionally and/or alternatively, some wasting stations take a significant amount of time to identify medications being wasted and/or to waste the medication being deposited into the waste container. For example, in some instances, the wasting process may take up to 30 minutes, an hour, or longer to identify the medication being wasted and/or to deposit the waste into the waste container. As described herein, the wasting system may waste (e.g., via an automated process and/or via a batch waste process) medication more efficiently and/or quickly, thereby reducing the resources required to waste medication and allowing users to perform additional tasks during the wasting process. This may also improve the user experience of the wasting system while wasting medication.

FIG. 1A depicts a system diagram illustrating a wasting system 100 consistent with implementations of the current subject matter. The wasting system 100 may be used, for example, for wasting medications (e.g., fluid and/or solid medications) after a medication has been dispensed, administered to a patient, and/or during one or more other wasting workflows. As used herein, the "wasting" of a medication may refer to the disposal of a substance in accordance with institutional guidelines and/or government regulations.

Referring to FIG. 1A, the wasting system 100 includes a wasting station 110, a user interface 130 accessible to a clinician 135, and a witnessing client 150 accessible to a witness 155. The user interface 130 and the witnessing client 150 may be communicatively coupled to the wasting station 110, for example, via a network. In some implementations, the user interface 130 and/or the witnessing client 150 may be part of and/or integrated with the wasting station 110. The wasting station 110, the user interface 130, and the witnessing client 150 may be implemented as or include processor-based devices, for example, a smartphone, a tablet computer, a wearable apparatus, a desktop computer, a laptop computer, a workstation, or the like. The network may be a wired and/or wireless network including, for example, a public land mobile network (PLMN), a local area network (LAN), a virtual local area network (VLAN), a wide area network (WAN), the Internet, a short range radio connection, for example a BLUETOOTH® compatible connection, a peer-to-peer mesh network, or the like.

In some implementations, the proper wasting of certain medications, such as prescription pain medications or other controlled substances, may require the controlled substance to be collected in a designated receptacle (e.g., the wasting station 110) while in the presence of one or more witnesses, such as the witness 155. In some implementations, the witnessing client 150 allows for the witness 155 to observe a wasting process and may provide for remote observation. The witnessing client 150 may be in communication with the wasting station 110 over one or more of: a local area network, a wireless connection, and a direct connection. The witnessing client 150 may include, for example, a laptop computer or a dedicated computer that allows a witness 155 to observe a wasting process taking place at the wasting station 110. The witnessing client 150 may be located near or at the wasting station 110. Alternatively, the witnessing client 150 may be remote, for example, at a physical location that is separate from the wasting station 110, allowing the witness 155 to observe the wasting process remotely, for example, using a camera on the wasting station 110. As such, the witnessing client 150 may reduce or eliminate the need to seek an authorized witness 155 to observe the wasting operation in real-time at the wasting station 110.

The witnessing client 150 may request credentials from the witness 155. For example, the witnessing client 150 may be prompted to enter a user name and password, scan a badge using a card reader, perform a fingerprint scan or a retina scan, and/or use facial recognition to identify the witness 155. The witnessing client 150 may transmit a control message to the wasting station 110 to collect the credential information. For example, the control message may activate a scanning device (e.g., camera, badge reader, optical scanner, etc.) associated with the wasting station 110 or cause display of a user interface to collect the credential information. The witnessing client 150 may include a display that is updated with actions performed by the clinician 135 during the wasting process. The witnessing client 150 may include the ability to communicate, view, and/or record the wasting process. Records captured at the witnessing client 150 may be stored and used during an audit of the wasting process.

Consistent with implementations of the current subject matter, the user interface 130 may be in communication with and/or form a part of the wasting station 110. For example, the user interface 130 may be integrated with at least a portion of the wasting station 110 and/or be coupled to the wasting station 110 via a local area network, a wireless connection, and/or a direct connection. The user interface 130 may include, for example, a display, a touch display, a keyboard, a mouse, one or more cameras, a card reader, a barcode scanner, a retina scanner, and/or a fingerprint scanner.

The wasting system 100 may include features to ensure coordination between the witnessing client 150 and the wasting station 110. For example, when remotely witnessing an event, the witness may require certain verifications that what is being witnessed and attested to is actually what is happening. Further, the wasting system 100 may coordinate the collection of event information (e.g., scans, credential presentation, authentication, authorization, waste container location, wasting station operational state, connectivity status (e.g., connection, disconnection, retry attempt), etc.). Accordingly, the wasting system 100 may include features to provide assurance to the users that the remote witnessing is secured and authentic along with features to capture and correlate the information collected by the separate devices (e.g., the witnessing client 150, the wasting station 110, and/or the like).

A user, such as a clinician 135 (e.g., a doctor, nurse, or other staff member or personnel), also referred to herein as a "user," may interact with the user interface 130 to access the functions of the wasting station 110. The user interface 130 may display prompts on the display and/or accept inputs from the clinician 135 to guide the clinician 135 through the wasting workflow, thereby confirming each step is complete, secure, and auditable.

The user interface 130 may authenticate the clinician 135 prior to allowing the clinician 135 to use the wasting station 110. For example, the user interface 130 may prompt the clinician 135 for a username and password or other identifying information. Alternatively or additionally, the user interface 130 may read the clinician's badge using a card reader. Alternatively or additionally, the user interface 130 may obtain biometric information from the clinician 135 including, for example, a retina scan, fingerprint scan, and/or facial recognition features.

Referring to FIG. 1A, the wasting station 110 may securely collect and store waste and/or one or more waste containers 125 as part of a wasting workflow. The wasting station 110 may be configured to receive and handle the waste, which as noted above, may be in the form of solids, liquids, medication dispensers, or applicators, such as syringes, patches, IV bags, and/or the like. Additionally and/or alternatively, the wasting station 110 may be configured to receive and handle one or more waste containers 125, in which the medication in the form of solids or liquids, or medication dispensers or applicators, is contained. The one or more waste containers 125 may include a bottle, a bin, and/or the like for receiving and storing the wasted medication. The waste container 125 may include one or more substances to neutralize the wasted medication held within the waste container 125.

In some implementations, as described in more detail below, the waste container 125 may be removable from the wasting station 110 by an authorized clinician or other personnel. The removal of the waste container 125 may be subject to authentication by the wasting station 110, where the authentication is a verification that the clinician (e.g., the clinician 135) or other personnel (e.g., the auditor 160) are authorized to handle the dispensed waste container. Such authentication may include, for example, prompting by the user interface 130 for the clinician 135 or the auditor 160 to enter a username and password or other identifying information. Alternatively or additionally, the user interface 130 may read the clinician's or the auditor's badge using a card reader. Alternatively or additionally, the user interface 130 may obtain biometric information from the clinician 135 or the auditor 160 including, for example, a retina scan, fingerprint scan, and/or facial recognition features. Authentication of the clinician 135 or other personnel may cause the wasting station 110 to disengage one or more locking systems, such as removal of an enclosure surrounding the waste container 125, actuation of a locking arm 311 to allow for removal of the waste container 125, release of a smart lock, and/or the like.

As shown in FIG. 1A, both an analysis facility 170 and a disposal facility 180 may be provided as part of the wasting system 100. Once the waste container 125 is removed from the wasting station 110, the waste container 125 may subsequently be transferred to one or more of the analysis facility 170 and/or the disposal facility 180. Such transfer may be performed by the clinician 135 or the auditor 160, for example, after authentication of the auditor 160, or other authenticated user. The transfer of the waste container 125 from the wasting station 110 may be tracked and recorded by the wasting station 110 as part of a record detailing the wasting process wasting the wasted medication. In particular, consistent with implementations of the current subject matter, the wasting station 110 may collect and store information about the wasting process. The stored information may be used during an audit to ensure compliance with rules and regulations governing the safe disposal of medications. The wasting process may include establishing a chain of custody for the waste container 125.

Figure 1B:
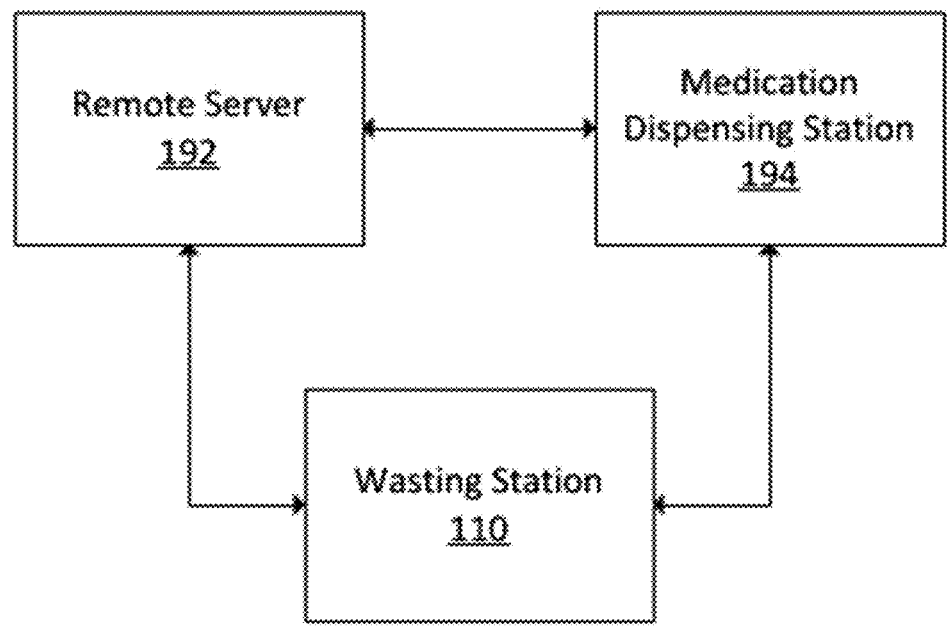

Referring to FIG. 1B, the wasting station 110 may be part of a system 190 that includes a remote server 192 and a medication dispensing station 194. The wasting station 110 and the medication dispensing station 194 may be an integrated unit or more be separate stations remote from one another. The wasting station 110, the remote server 192, and the medication dispensing station 194 may be communicatively coupled to one another via a network. The network may be a wired and/or wireless network including, for example, a public land mobile network (PLMN), a local area network (LAN), a virtual local area network (VLAN), a wide area network (WAN), the Internet, a short range radio connection, for example Bluetooth, a peer-to-peer mesh network, and/or the like. The remote server 192 may provide data and/or instructions to the wasting station 110 to implement one or more features of the wasting process consistent with implementations of the current subject matter. For example, the remote server 192 may coordinate the communication session between the wasting station 110 and a witnessing client. Additionally and/or alternatively, the remote server 192 may cause the wasting station 110 to begin, continue, and/or stop one or more wasting processes.

Figure 2:
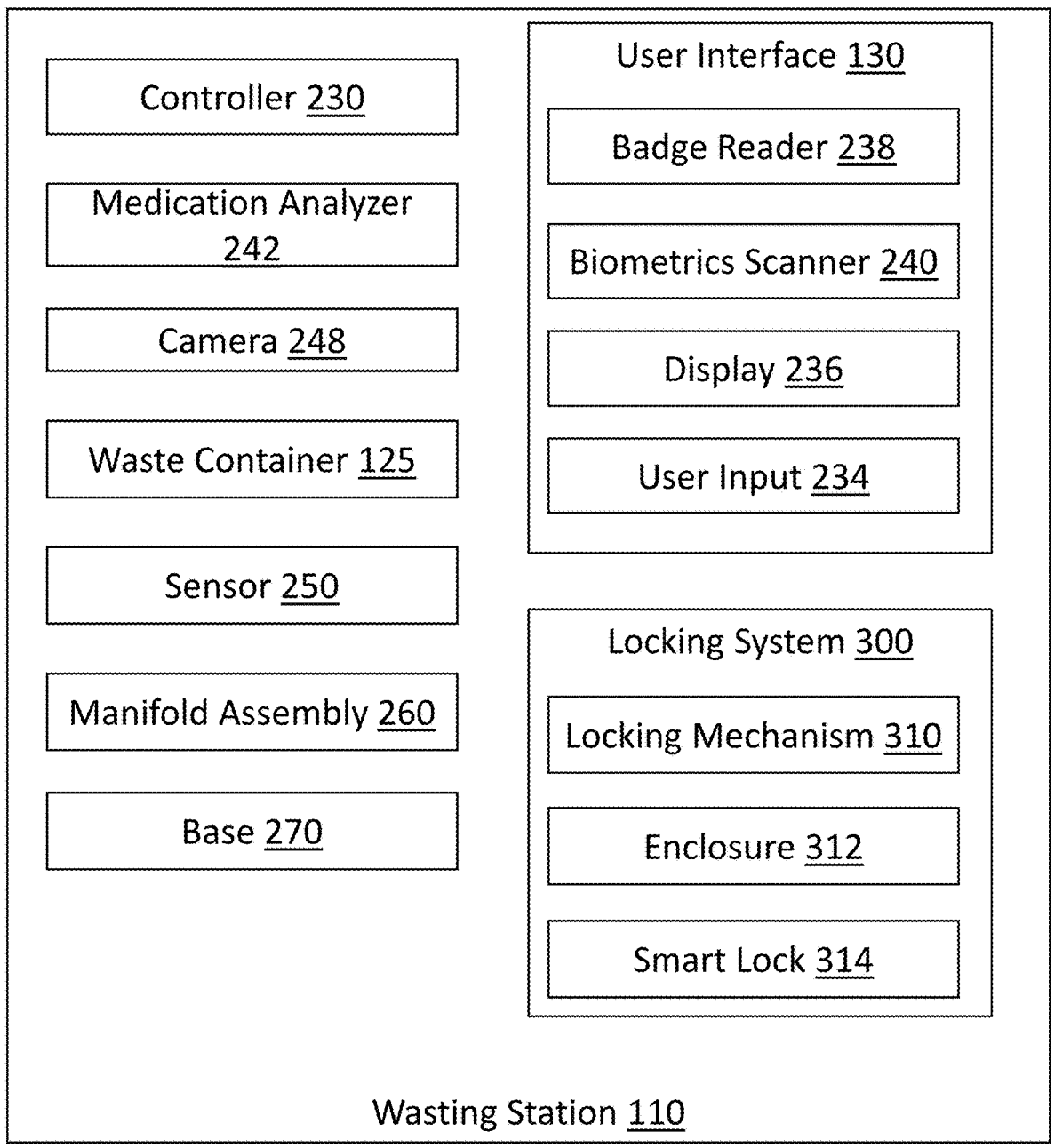
FIG. 2 is a block diagram depicting aspects of a wasting system, consistent with implementations of the current subject matter.
Figure 3:
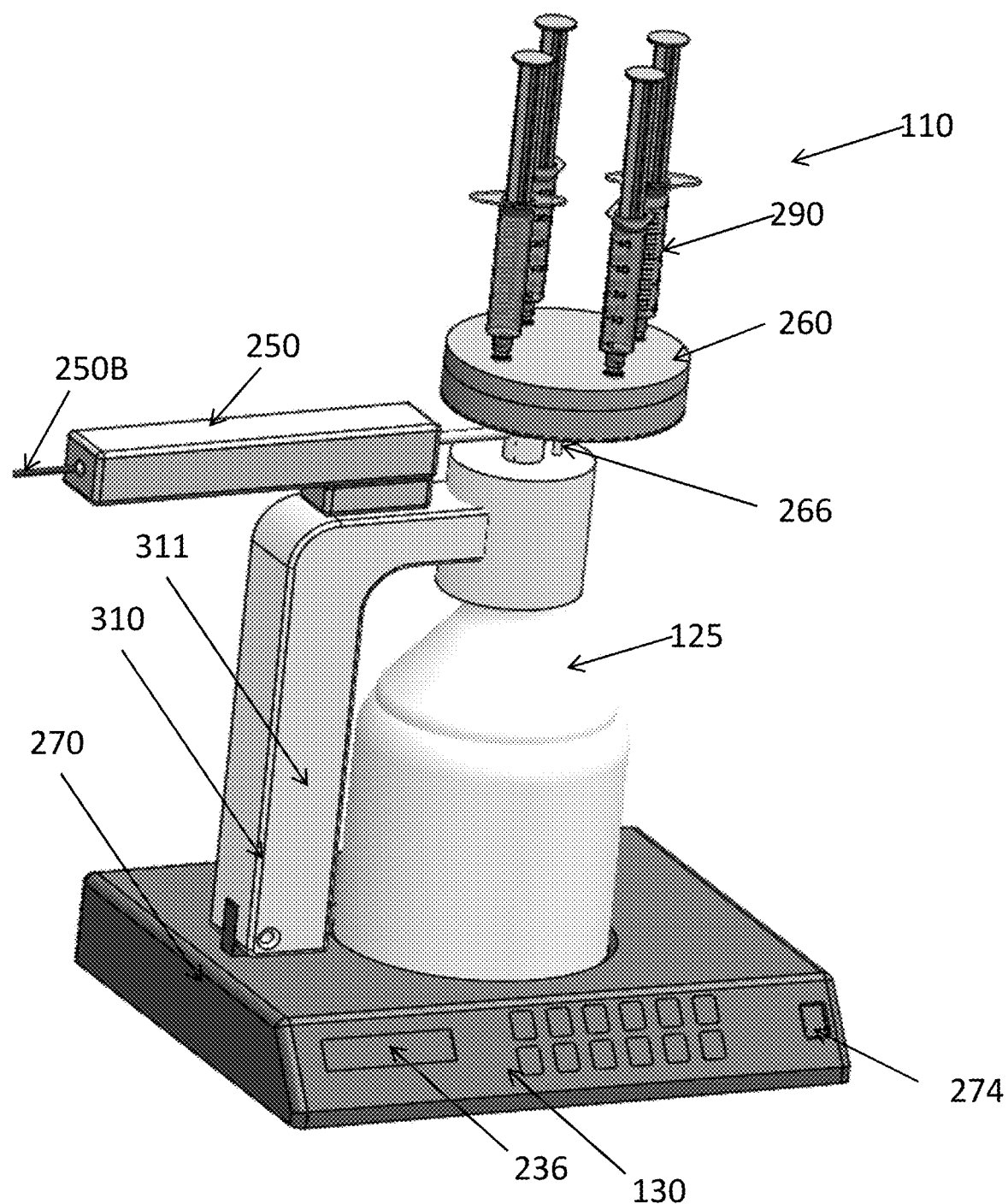
FIG. 3 depicts an example wasting station, consistent with implementations of the current subject matter.

FIG. 2 is a block diagram depicting aspects of the wasting station 110, consistent with implementations of the current subject matter.

The wasting station 110 may include a controller 230 which controls one or more functions of the wasting station 110. The controller 230 may include, for example one or more processors, one or more computers, one or more programmable logic controllers, and/or the like. The controller 230 may include actuators, for example, motors, solenoids, and/or the like. The controller 230 may use the actuators to move mechanisms, such as a locking system 300, a manifold assembly 260, a sequencing mechanism (e.g., sequencing mechanism 266, 866), a plunger mechanism 868, a medication dispenser, and/or the like into a desired position. The controller 230 may include or be coupled to one or more sensors 250, for example, limit switches, flow sensors, optical sensors, tachometers, encoders, load cells, weight sensors, torque sensors, and/or the like. The controller 230 may use the sensors 250 to detect whether a mechanism, such as the locking system, manifold assembly, sequencing mechanism, plunger mechanism and/or medication dispenser is, for example, in position, out of position, moving, applying a force, applying a torque, and/or the like. The wasting station 110 may also include the user interface 130 (which may include a badge reader 238, a biometrics scanner 240, a display 236, a user input 234, and/or the like), the locking system 300 (which may include a locking mechanism 310, an enclosure 312, a smart lock 314, and/or the like), an medication analyzer 242, a camera 248, the waste container 125, a sensor 250, a manifold assembly 260, and a base 270, which are described in more detail below.

The manifold assembly 260 may receive one or more medication dispensers, such as syringes. For example, as shown in FIGS. 3-6, the manifold assembly 260 may include one, two, three, four, five, six, seven, eight, or more slots, in which at least a portion of the medication dispensers may be coupled and/or inserted. The manifold assembly 260 may include an interior cavity, which collects the medication dispensed from at least one of the medication dispensers. The interior cavity may hold at least a portion of the dispensed medication for a period of time (e.g., 1 to 10 seconds, 1 to 30 seconds, 1 to 60 seconds, 1 to 2 minutes, 1 to 10 minutes, 1 to 30 minutes, 1 to 60 minutes, 1 to 120 minutes and/or other ranges therebetween). In other implementations, the interior cavity defines a channel through which the dispensed medication passes from the medication dispenser to the waste container 125. The manifold assembly 260 may be positioned above the waste container 125 to allow the wasted medication to pass from the medication dispenser to the waste container 125 or the interior cavity more easily, such as via gravity, or physical manipulation of the medication dispenser (e.g., depression of a syringe, squeezing an IV bag, and/or the like). In some implementations, the manifold assembly 260 includes one or more valves to allow the medication to pass from the medication dispenser into the interior cavity, and/or from the interior cavity to the waste container 125. The manifold assembly 260 may include a sequencing mechanism that rotates and/or otherwise moves the manifold assembly 260 into the proper position such that the medication dispenser is appropriately located above the waste container 125. As described herein, the manifold assembly 260 may rotate and/or move so that each medication dispenser may dispense the wasted medication at the appropriate time, such as when each medication dispenser is in the proper position to waste the wasted medication.

As noted above, the waste container 125 may include a bottle, a bin, and/or the like for receiving and storing the wasted medication. The waste container 125 may be removably positioned on the base 270. The base 270 may support the waste container 125 and/or the locking system 300. The base 270 may include one or more sensors 250 and/or the user interface 130. For example, the one or more sensors 250 may include one or more weight sensors or load cells 250A. The one or more weight sensors 250A may be positioned on or may be integrated with the base 270. In some implementations, the one or more weight sensors 250A may measure and/or calculate a weight of the medication wasted and deposited into the waste container 125. For example, the one or more weight sensors 250A may measure a total weight of the waste container 125 and the waste deposited into the waste container 125. In such implementations, the controller 230 may remove a weight of the waste container 125 from the total weight of the waste container 125 and the waste deposited into the waste container 125 to determine the actual weight of the waste deposited into the waste container 125. In some implementations, the weight of the waste container 125 is predetermined. In other implementations, the one or more weight sensors 250A measures a weight of the waste container 125 before any waste is deposited into the waste container 125 to obtain the weight of the waste container 125. In some implementations, the controller 230 and/or the one or more weight sensors 250A measures a change in the total weight to determine the actual weight of the waste deposited into the waste container 125, such as after each medication dispenser is emptied into the waste container 125.

In some implementations, the controller 230 determines a volume of the wasted medication that has been deposited into the waste container 125 based on the total weight, the actual weight of the wasted medication deposited into the waste container 125, the change in the total weight, and/or the like. As explained in more detail herein, based on the measured and/or calculated weight and/or volume of wasted medication, the wasting station 110 (e.g., via the controller 230) may determine whether a diversion of medication has occurred. For example, the controller 230 may compare the measured and/or calculated weight and/or volume of wasted medication with an expected weight and/or volume of wasted medication to verify whether the expected weight and/or volume is equal to the measured and/or calculated weight and/or volume. If the measured weight and/or volume of wasted medication is equal to or is within an acceptable range (e.g., within 0.25 mL to 0.5 mL, 0.5 mL to 0.75 mL, 0.75 mL to 1.0 mL, 1.0 mL to 5 mL and/or other ranges therebetween) of the expected weight and/or volume of wasted medication, the controller 230 may determine that no diversion has occurred. Alternatively, if the measured weight and/or volume of wasted medication is not equal to or is not within an acceptable range (e.g., within 0.25 mL to 0.5 mL, 0.5 mL to 0.75 mL, 0.75 mL to 1.0 mL, 1.0 mL to 5 mL and/or other ranges therebetween) of the expected weight and/or volume of wasted medication, the controller 230 may determine that a suspected diversion has occurred.

Based on the detection of a suspected diversion, the controller 230 may flag the waste process for further review, and/or may store, or transmit to a database, various aspects of the wasting process, such as the clinician ID, the type of medication wasted, the expected weight and/or volume of wasted medication, the measured weight and/or volume of wasted medication, and/or the like. Flagging an item for review may include storing, in a data storage device, a review indicator for the waste process. Additionally and/or alternatively, the controller 230 may trigger an alert (e.g., an audio, visual, message, or other alert) upon the detection of suspected diversion. In other implementations, however, an alert generated at the wasting station 110 may not be generated. Instead, an alert may not be generated and/or an alert may be generated at a remote location to warn a supervisor, auditor, and/or other personnel. As a result, the clinician 135 may not know whether the wasted medication is being flagged for audit, providing an incentive for the clinician 135 to not engage in diversion of medications. Accordingly, the wasting station 110 including the weight sensor 250A described herein more accurately measures a volume of medication that has been wasted and actually deposited into the waste container 125.

In some implementations, to determine whether a diversion and/or suspected diversion of medication has occurred, the wasting station 110 (e.g., the controller 230) may take into account one or more factors, such as the difference between the expected weight and/or volume of wasted medication and the measured weight and/or volume of wasted medication, the wasting user, the witnessing user, a wasting location, the substance (e.g., medication) being wasted, or other properties detectable or accessible by the wasting station 110. For example, if the substance being wasted is an uncontrolled solid (e.g., excess ibuprofen) or liquid (e.g., excess acetaminophen), the risk of diversion may be less than when wasting a controlled substance such as oxycodone, fentanyl, and/or the like. In some implementations, a risk score may be generated based on one or more of the factors described herein, such as the difference between the expected weight and/or volume of wasted medication and the measured weight and/or volume of wasted medication, the wasting user, witnessing user, wasting location, substance being wasted, or other property detectable or accessible by the wasting station 110. If the risk score corresponds to (e.g., is greater than, less than, or equal to) a threshold, the substance being wasted may be flagged for later audit and/or an alert may be generated. Features for generating risk scores are described in, for example, U.S. Patent Publication No. US20170109497A1 entitled "Controlled substance diversion detection systems and methods," commonly owned and assigned, which is incorporated by reference in its entirety.

Referring to FIG. 2, the user interface 130 may include a badge reader 238, a biometrics scanner 240, a display 236, a user input 234, and/or the like. The user interface 130 may be coupled to or integrated with the wasting station 110, such as the base 270 of the wasting station 110. In some implementations, at least a portion of the user interface 130 forms a part of the wasting station 110, and at least a portion of the user interface 130 is coupled to an external client device, such as a computer, mobile phone, and/or the like, which is communicatively coupled to the wasting station 110.

The user interface 130 may receive data that is used for a later audit of the wasted medication at the wasting station 110. For example, the wasting station 110 may include one or more auditing features. The one or more auditing features may be features that allow for the wasted medication and/or the waste container 125 to be tracked and associated with a user, such as the clinician 135. For example, the wasting station 110 may record information collected when the waste is deposited, including the identification tag (barcode, RFID tag, etc.) of the clinician 135 and/or the identity of the clinician 135 who deposited the waste, videos recorded during the wasting process, and physical property measurements taken during the wasting process. The user interface 130 may provide the badge reader 238 for reading an identification code of the clinician 135 and/or the biometrics scanner 240 for obtaining biometric features of the clinician 135. The identification code of the clinician 135 and/or the biometric features of the clinician may be received by the user interface 130 and be stored as a part of a record. The record may be linked to or associated with the clinician 135 for tracking and later auditing. The record may also include time and date details to associate timing with the wasting process.

In some implementations, the user interface 130 includes a display 236. The display 236 may display one or more measured and/or calculated aspects during the wasting process. For example, the display 236 may display a weight and/or a volume of the wasted medication deposited into the waste container 125 and/or a total weight of the wasted medication and the waste container 125. In some implementations, the display 236 presents the type of medication deposited into the waste container 125.

Referring again to FIG. 2, the user interface 130 includes a user input 234. The user input 234 may include dials, buttons, icons, selectable areas, or other perceivable indicia presented via the user interface 130 that, when interacted with (e.g., clicked, touched, selected, etc.), initiates an exchange of data for the wasting station 110 to present via the user interface 130. For example, the user input 234 may receive information about the medication being wasted, such as an expected volume and/or weight of the medication to be wasted and deposited into the waste container 125 and/or a type of medication to be wasted and deposited into the waste container 125.

In some implementations, the wasting station 110 includes one or more cameras 248. The camera 248 may be used to monitor and/or record the wasting process, including recording video of the user who places or otherwise connects the medication dispenser to the wasting station 110 and/or deposits the wasted medication into the wasting station 110. One or more cameras 248 may be used to record video of the waste item as it is placed in the waste container 125 and/or coupled to the wasting station 110. In some implementations, the one or more cameras 248 may be used for image analysis of a medication and/or medication dispenser. Image analysis of the medication and/or medication dispenser may include identification of medications based on, for example, color, size, shape, and/or markings on the medication and/or medication dispenser.

Consistent with implementations of the current subject matter and as shown in FIG. 2, the wasting station 110 may include a medication analyzer 242. The medication analyzer 242 may analyze the wasted medication. The medication analyzer 242 may be integrated with and/or be coupled to one or more of the sensors 250, such as a medication analysis sensor 250B, such as a flow sensor, an optical sensor, and/or a spectrometer. The sensor 250B and/or the medication analyzer 242 may be positioned between the manifold assembly 260 and the waste container 125 such that the wasted medication passes through and/or around the sensor 250B from the manifold assembly 260 and/or the medication dispenser to the waste container 125. In other words, the sensor 250B is positioned along a flow path of the wasted medication from the manifold assembly 260 and/or the medication dispenser to the waste container 125, and the wasted medication contacts the sensor 250B. The sensor 250B may measure one or more aspects of the medication as the medication contacts and/or passes the sensor 250B. For example, the sensor 250B may measure a flow rate, a volume of medication that passes the sensor 250B, a type of medication, a color for the medication, and/or the like.

In some implementations, the medication analyzer 242 may be separate and/or remote from the base 270, the waste container 125, and/or the manifold assembly 260. In other implementations, the medication analyzer 242 forms a part of at least one of the base 270, the waste container 125, and/or the manifold assembly 260. As noted above, the medication analyzer 242 may perform analysis of liquid and/or solid wasted medication. For example, the medication analyzer 242 and/or the sensor 250B may perform, on a wasted medication, Raman spectroscopy, refractometry, image analysis (e.g., color, size, shape, markings, and/or the like), and/or the like to determine the type of medication being wasted. This may be useful to verify that the medication being wasted matches the type of medication expected to be wasted based on, for example, the type of medication received via the user interface 130. In some implementations, the medication analyzer 242 holds at least a portion of the wasted medication as the wasted medication passes between the manifold assembly 260 and the waste container 125 to perform the analysis, such as via the sensor 250B. In other implementations, the medication analyzer 242 and/or the sensor 250B performs analysis of the wasted medication as the wasted medication passes between the manifold assembly 260 and the waste container 125. In some implementations, the medication analyzer 242 and/or the sensor 250B measures one or more aspects of the wasted medication at various times during the wasting process, such as at the beginning, middle, and end of the wasting process to confirm that the same medication is being wasted throughout the entire wasting process. This helps to prevent or reduce the likelihood of diversion as it may be more difficult for users to remove the medication being wasted and/or replace the medication with another substance during the wasting process.

As noted above, the wasting station 110 may include one or more sensors 250, such as the sensors 250A, 250B. Each of the one or more sensors 250 may be positioned at various locations on and/or in the wasting station 110, such as between the manifold assembly 260 and the waste container 125, along the flow path of the wasted medication, at the base 270, and/or the like. The one or more sensors 250 may measure one or more properties (e.g., physical properties) of the wasted medication and/or the waste container 125 as the wasted medication is being deposited, stored, and/or analyzed. For example, the one or more sensors 250 may include one or more flow rate sensors, color sensors, density sensors, scales, load cells, weight sensors, spectrometers, optical sensors, temperature sensors, and/or other sensors.

Referring again to FIG. 2, the wasting station 110 may include a locking system 300. The locking system 300 may include one or more locking features, such as a locking mechanism 310, an enclosure 312, and a smart lock 314, which help to secure the waste container and/or the wasting process. The locking features may help to limit or prevent diversion of the wasted medication at various stages of the wasting process by, for example, limiting access to and/or the removal of the waste container 125, the one or more sensors 250, and/or the like, to authorized personnel, such as personnel that have been verified by the wasting station 110 and/or personnel whose credentials have been received and/or stored by the wasting station 110 for later audit.

In some implementations, the locking mechanism 310 includes a locking arm 311 that may be mounted on a surface of the wasting station 110. For example, at least one end of the locking arm 311 may be rotatably coupled to the base 270 of the wasting station 110. The locking arm 311 may include another end that is coupled to and/or surrounds an open end of the waste container 125 when the wasting station 110 is in a first or locked position. Upon receipt of credentials of an authorized user, the wasting station 110 (e.g., via the controller 230) may transmit a command to move the locking arm 311 to a second or unlocked position. For example, the locking arm 311 may pivot or rotate (e.g., about a hinge) from the first position away from the waste container 125 to provide access to the waste container 125 in the second position for removal. Thus, in the second position, the waste container 125 may be detached and/or removed from the wasting station 110. In some implementations, the manifold assembly 260 and/or one or more of the sensors 250 are coupled to and/or are supported by a portion of the locking arm 311. In such implementations, the manifold assembly 260 and/or one or more of the sensors 250 move from the first position to the second position together with the locking arm 311 when the user is authorized to remove the waste container 125. The locking arm 311 of the locking mechanism 310 helps to ensure that only an authorized user is provided access to the waste container 125 and/or its contents, such as during removal of the waste container 125 from the wasting station 110. This helps to limit or prevent diversion of the wasted medication.

Additionally and/or alternatively the locking system 300 includes the enclosure 312. The enclosure 312 surrounds at least a portion of the wasting station 110, such as at least the waste container 125 during the wasting process. Similar to the locking arm 311, upon receipt of credentials of an authorized user, the wasting station 110 (e.g., via the controller 230) may transmit a command to move the enclosure from a first or locked position in which the enclosure surrounds at least the waste container 125 to a second or unlocked position. The enclosure 312 helps to ensure that only an authorized user is provided access to the waste container 125 and/or its contents, such as during removal of the waste container 125 from the wasting station 110. This help to limit or prevent diversion of the wasted medication.

Additionally and/or alternatively, the locking system 300 includes a smart lock 314, which may be separate from and/or integrated with one or more of the other locking features, such as the locking mechanism 310 and/or the enclosure 312. The smart lock 314 may be configured to release or engage based on multiple factors that are dynamically assessed. For example, the smart lock 314 may be applied to the waste container 125 of the wasting station 110. The smart lock 314 may include location awareness to determine a current location of the smart lock 314. The smart lock 314 may consider the location along with the credentials of a user when the user requests access to the locked element. The smart lock 314 may determine, based on the location and/or user credentials, whether to release the smart lock 314. This ensures that only authorized personnel are allowed to access the locked element (e.g., the waste container 125), and that such access only takes place in an appropriate location and/or at an appropriate time (e.g., at the end of a wasting process). The smart lock 314 may include additional and/or other sensors. For example, the smart lock 314 may include a temperature sensor to record the environment around the locked element. This temperature information may affect the results of tests performed on waste items stored in the locked element. The smart lock 314 may include a memory element to store the sensor, location, time, and/or other information detected or generated by the smart lock 314. The smart lock 314 may include a communications module for transmitting sensor data along with access requests. Thus, if the clinician 135 is suspected of diverting medications, the wasting station 110 may flag for an audit the wasted medication and/or the waste container 125.

FIGS. 3-6 illustrate an example of the wasting station 110 including the base 270 including one or more of the sensors 250 such as the weight sensor, the waste container 125, the locking system 300, the medication analyzer 242 including one or more sensors 250 such as the flow sensor and/or the optical sensor, and/or the manifold assembly 260.

Figure 4:
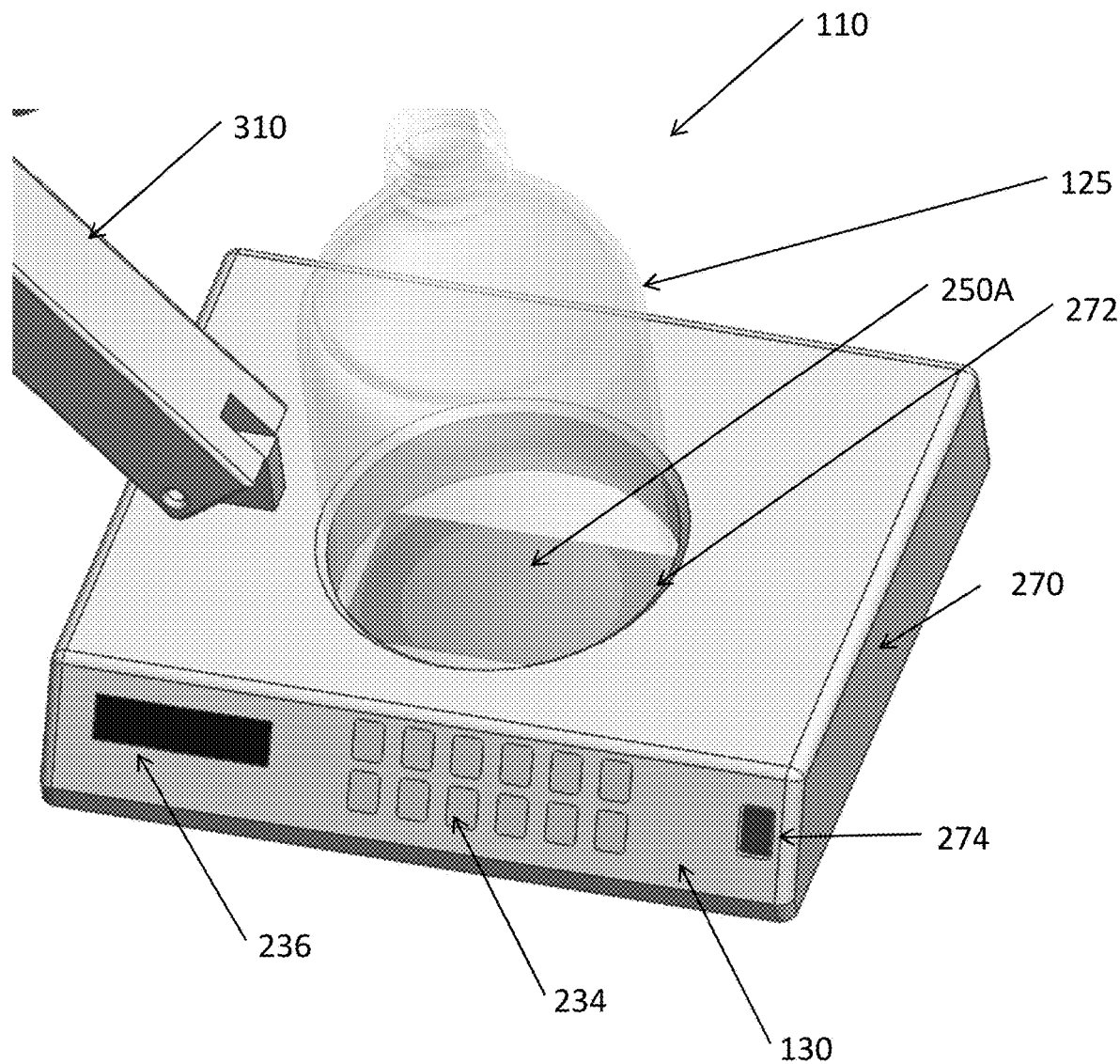
FIG. 4 depicts a portion of an example wasting station, consistent with implementations of the current subject matter.

FIG. 4 illustrates a close-up view of the base 270, consistent with implementations of the current subject matter. The base 270 may support the locking mechanism 310 and/or the waste container 125. For example, the base 270 may include a recess 272 in which a portion of the waste container 125 is supported. The recess 272 helps to secure at least a portion, such as a bottom portion, of the waste container 125, to prevent or limit unauthorized removal of the waste container 125 from the wasting station 110. In other implementations, the base 270 does not include the recess 272, and instead includes a flat surface that supports the waste container 125.

The recess 272 (or another portion of the base 270 upon which the waste container 125 is supported) may include one or more sensors, such as a weight sensor (e.g., a sensor, scale, and/or load cell) 250A. The weight sensor 250A may be positioned on and/or may be integrated with a portion of the base 270, such as a bottom surface of the recess 272. The one or more weight sensors 250A may measure and/or calculate a weight of the medication wasted and deposited into the waste container 125. For example, the one or more weight sensors 250A may measure a total weight of the waste container 125 and the waste deposited into the waste container 125. As described herein, the controller 230 may remove a weight of the waste container 125 from the total weight of the waste container 125 and the waste deposited into the waste container 125 to determine the actual weight of the waste deposited into the waste container 125. In some implementations, the controller 230 and/or the one or more weight sensors 250A measures a change in the total weight to determine the actual or measured weight of the waste deposited into the waste container 125, such as after each medication dispenser is emptied into the waste container 125.

Referring to FIG. 4, the base 270 includes the user interface 130. The user interface 130 includes a display 236, which may display a weight and/or a volume of the wasted medication deposited into the waste container 125 and/or a total weight of the wasted medication and the waste container 125. The display 236 may additionally and/or alternatively present a volume remaining in the waste container 125. In some implementations, the controller 230 of the wasting station 110 may determine that no more medication may be wasted into the waste container 125, such as when the waste container 125 is full or has reached a predefined maximum weight and/or volume, or that no more medication may be wasted into the waste container 125 within an amount of time (e.g., 1 minute, 5 minutes, 10 minutes, 30 minutes, 1 hour, and/or the like). In such implementations, the controller 230 may determine that no more medication may be wasted into the waste container 125 based on the weight and/or volume of the medication already wasted into the waste container 125. The controller 230 may generate, via the user interface 130, one or more perceivable alerts (visual, audio, and/or the like), that indicate that the waste container 125 should be removed and no more medication should be wasted into the waste container 125.

Additionally and/or alternatively, the user interface 130 includes a user input 234. The user input 234 may include dials, buttons, icons, selectable areas, or other perceivable indicia presented via the user interface 130 that, when interacted with (e.g., clicked, touched, selected, etc.), initiates an exchange of data for the wasting station 110 to present via the user interface 130. For example, the user input 234 may receive information about the medication being wasted, such as an expected volume and/or weight of the medication to be wasted and deposited into the waste container 125 and/or a type of medication to be wasted and deposited into the waste container 125. The information about the medication being wasted may be entered by the user before the wasting process. The controller 230 may compare one or more measurements, such as an identified type of medication and/or a measured volume of wasted medication to the entered information about the medication, such as the type of medication and/or the expected volume of wasted medication, to determine whether a diversion has occurred, and/or a suspected diversion has occurred.

Additionally and/or alternatively, the user interface includes an authentication feature 274, such as one or more a badge reader for reading an identification code of the clinician 135 and/or a biometrics scanner for obtaining one or more biometric features of the clinician 135. The authentication feature 274 may authenticate a user before, during, and/or after medication has been wasted and deposited into the wasting station 110. In some implementations, upon verification of the user, such as via the authentication feature 274, the locking mechanism 310 may move from a locked position to an unlocked position, allowing the authorized user to remove the waste container 125.

Figure 5:
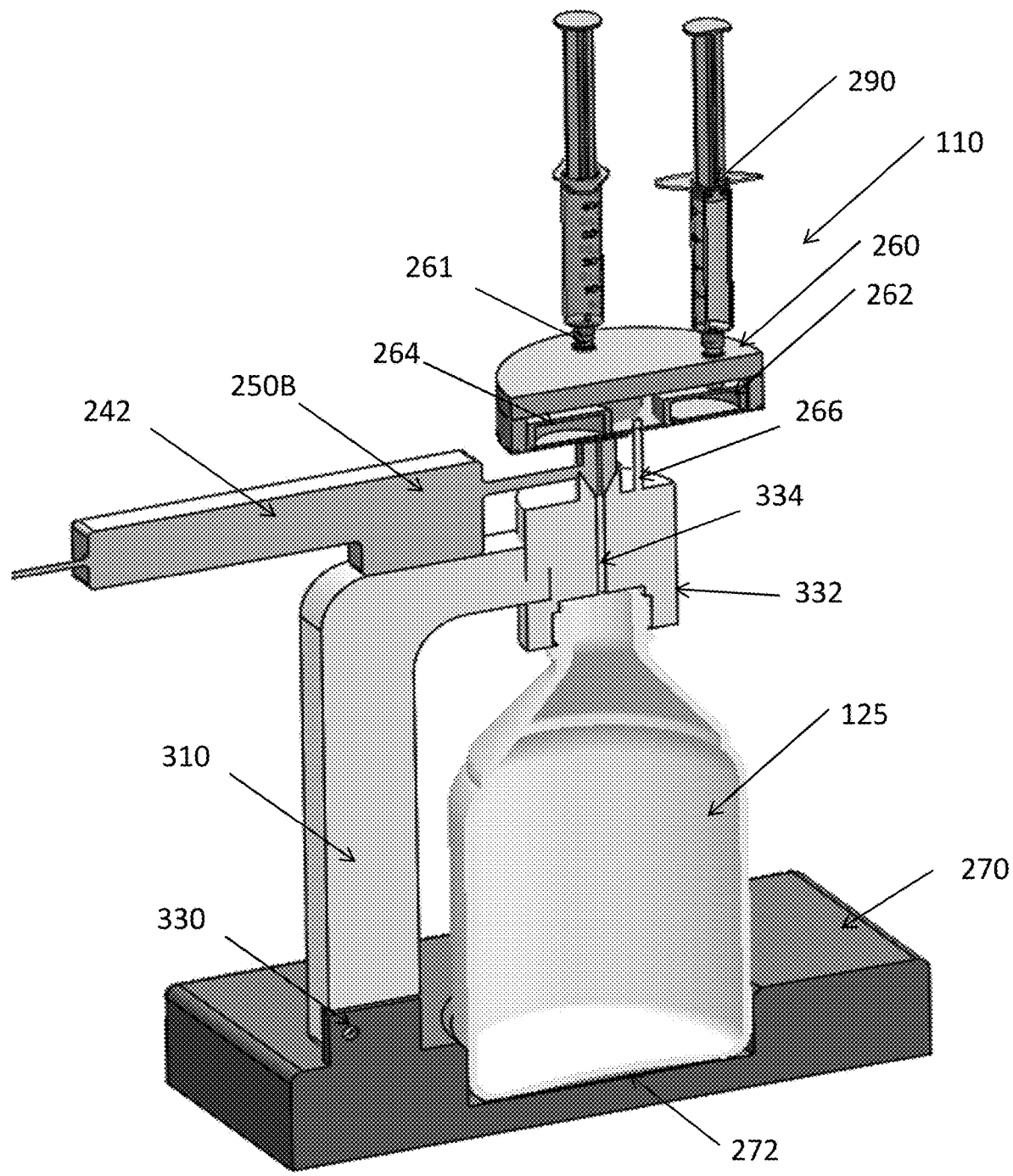
FIG. 5 depicts a cross-sectional view of an example wasting station, consistent with implementations of the current subject matter.

FIG. 5 illustrates cross-sectional view of the wasting station 110, consistent with implementations of the current subject matter. As shown in FIG. 5, the wasting station 110 includes a locking mechanism 310. The locking mechanism 310 secures the waste container 125 during the wasting process to limit or prevent diversion of the wasted medication at various stages of the wasting process by, for example, limiting access to and/or the removal of the waste container 125, the one or more sensors 250, and/or the like, to authorized personnel, such as personnel that have been authorized by the wasting station 110 and/or personnel whose credentials have been received and/or stored by the wasting station 110 for later audit.

In some implementations, the locking mechanism 310 includes a locking arm 311 that may be coupled to the base 270. For example, the locking mechanism 310 may include a first end 330 pivotably coupled to the base 270, and a second end 332 coupled to an open end of the waste container 125. For example, the waste container 125 may include an open end that is configured to receive the wasted medication, and a closed end opposite the open end. The closed end may be positioned within the recess of the base 270. The second end 332 of the locking mechanism 310 may cover and/or surround at least a portion of the open end of the waste container 125 to prevent access to the contents of the waste container 125.

As shown in FIG. 5, the second end 332 may include a channel 334. The channel 334 extends through the second end 332 of the locking mechanism 310 to define at least a portion of the flow path between the medication dispenser and the waste container 125. For example, the channel 334 may be in fluid communication with the manifold assembly 260 and/or the medication dispenser. Accordingly, the second end 332 of the locking mechanism 310 alone, or together with the manifold assembly 260, provides a closed system that allows the wasted medication to pass from the medication dispenser to the waste container 125 without allowing access to the wasted medication along the flowpath between the medication dispenser and the waste container 125. Thus, the wasting station 110 described herein securely stores the wasted medication and helps to prevent or limit diversion of the wasted medication.

Figure 6:
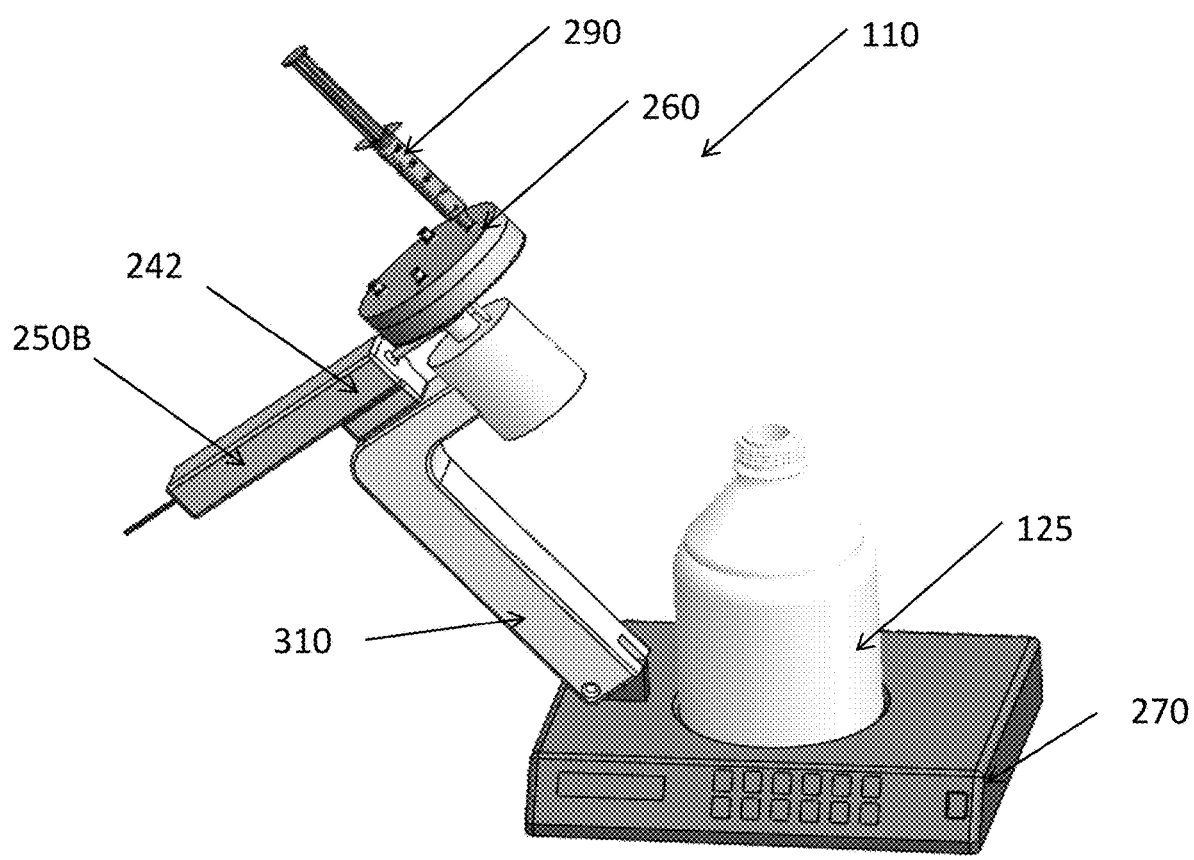
FIG. 6 depicts an example wasting station, consistent with implementations of the current subject matter.

In some implementations, upon receipt of credentials of an authorized user, such as via the user interface 130, the wasting station 110 (e.g., via the controller 230) may transmit a command to move the locking arm 311 from a first locked position (see FIGS. 3 and 5) to a second or unlocked position (see FIG. 6). For example, the locking arm 311 may move (e.g., rotate, pivot, slide, and/or the like) from the first position away from the waste container 125 to provide access to the waste container 125 in the second position, for removal. Thus, in the second position, the waste container 125 may be detached and/or removed from the wasting station 110. The locking mechanism 310 helps to ensure that only an authorized user is provided access to the waste container 125 and/or its contents, such as during removal of the waste container 125 from the wasting station 110. This help to limit or prevent diversion of the wasted medication.

In some implementations, the locking mechanism 310 supports the manifold assembly 260 and/or the one or more sensors 250. For example, the manifold assembly 260 and/or one or more of the sensors 250 may move from the first position to the second position together with the locking mechanism 310 when the user is authorized to remove the waste container 125.

Referring to FIGS. 3-6, the wasting station 110 also includes the medication analyzer 242, which may analyze the wasted medication. The medication analyzer 242 may be integrated with and/or be coupled to one or more of the sensors 250, such as a medication analysis sensor 250B, such as a flow sensor, an optical sensor, and/or a spectrometer. The sensor 250B and/or the medication analyzer 242 may be positioned between the manifold assembly 260 and the waste container 125 such that the wasted medication passes through and/or around the sensor 250B from the manifold assembly 260 and/or the medication dispenser to the waste container 125. In other words, the sensor 250B is positioned along a flow path of the wasted medication from the manifold assembly 260 and/or the medication dispenser to the waste container 125, and the wasted medication contacts the sensor 250B. The sensor 250B may measure one or more aspects of the medication as the medication contacts and/or passes the sensor 250B. For example, the sensor 250B may measure a flow rate, a volume of medication that passes the sensor 250B, a type of medication, and/or the like.

The medication analyzer 242 may perform an analysis of the wasted medication, to determine the type of medication being wasted. This may be useful to verify that the medication being wasted is the same as the type of medication expected to be wasted, based on, for example, the type of medication received via the user interface 130. In some implementations, the medication analyzer 242 holds at least a portion of the wasted medication to perform the analysis, such as via the sensor 250B. In other implementations, the medication analyzer 242 performs the analysis of the wasted medication as the wasted medication passes along the flow path between the manifold assembly 260 and the waste container 125. In some implementations, the medication analyzer 242 and/or the sensor 250B measures one or more aspects of the wasted medication at various times during the wasting process, such as at the beginning, middle, and end of the wasting process to confirm that the same medication is being wasted throughout the entire wasting process. This helps to prevent or reduce the likelihood of diversion as it may be more difficult for users to remove the medication being wasted and/or replace the medication with another substance during the wasting process.

Figure 9:
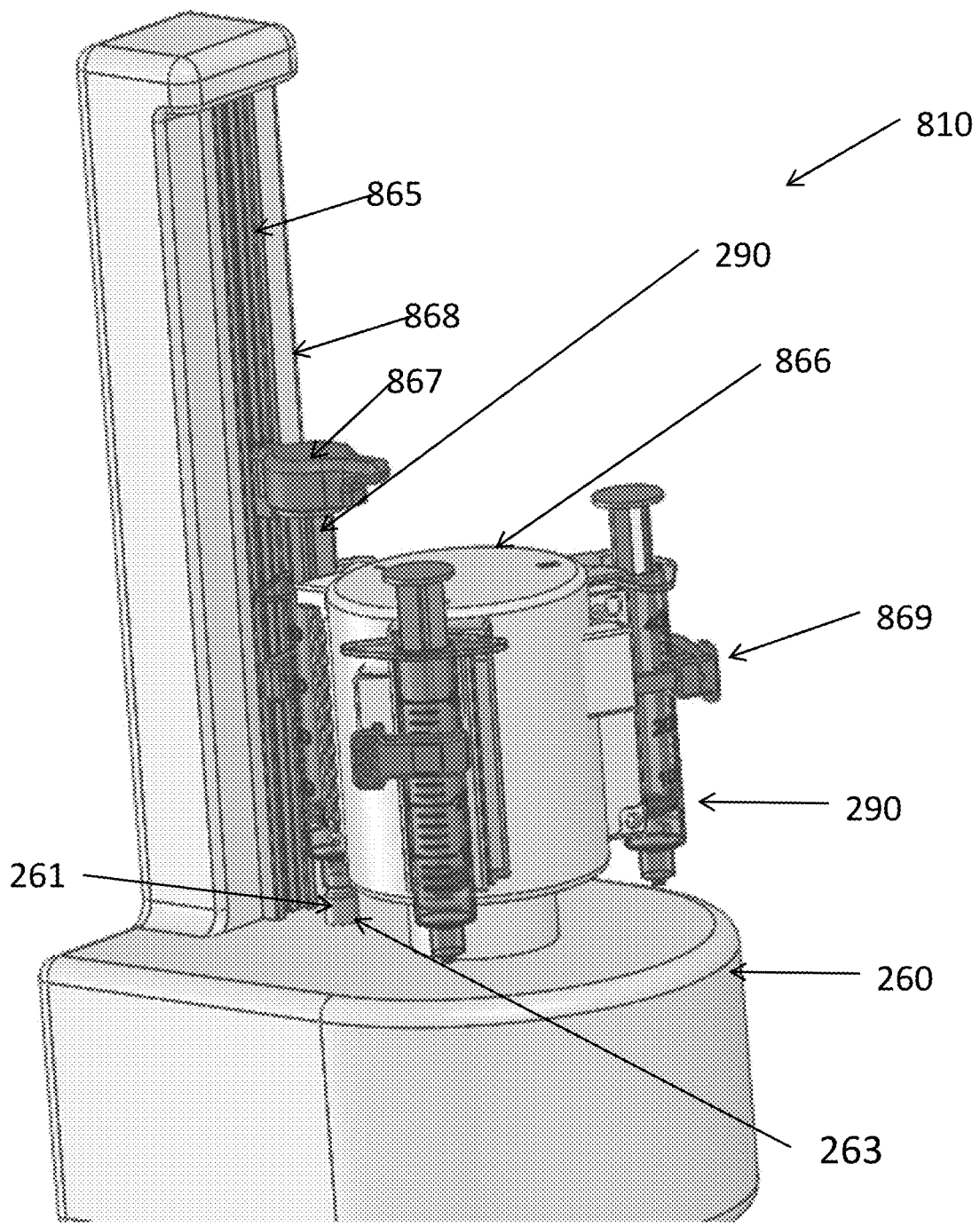
FIG. 9 depicts a portion of an example wasting station, consistent with implementations of the current subject matter.

As shown in FIGS. 3-6, one or more medication dispensers 290, such as one or more syringes, may be coupled to the wasting station 110. In particular, the one or more medication dispensers 290 may be coupled to the manifold assembly 260. The manifold assembly 260 may be cylindrical, rectangular, oval, and/or have another shape. The manifold assembly 260 shown in FIGS. 3-6 includes four slots 261, each configured to receive at least a portion, such as a tip end, of a corresponding medication dispenser 290. The slots 261 may form openings that extend through an outer surface of the manifold assembly 260. In some implementations, the manifold assembly 260 includes one, two, three, four, five, six, seven, eight, or more slots 261, each of which receive a corresponding medication dispenser 290. In some implementations, the slots 261 include a coupling feature 263 (see FIGS. 7 and 9) that is configured to receive at least a portion of the medication dispenser 290.

FIG. 5 illustrates a cross-sectional view of the wasting station 110, showing an interior of the manifold assembly 260. The manifold assembly 260 includes an interior cavity 262. The interior cavity 262 may include one or more compartments 264. In some implementations, the one or more compartments 264 includes a single compartment occupying the entire interior cavity 262 that is configured to receive the medication dispensed from at least one of the medication dispensers 290. In other implementations, the one or more compartments 264 includes one, two, three, four, five, six, seven, eight, or more compartments 264, which correspond to each of the slots 261. For example, each of the one or more compartments 264 may be positioned below and/or adjacent to a corresponding slot 261. The one or more compartments 264 of the interior cavity 262 collect the wasted medication dispensed from each corresponding medication dispenser 290.

Each of the one or more compartments 264 may be configured to hold all or a portion of the medication dispensed from one or more of the medication dispensers 290. As described above, the one or more compartments 264 of the interior cavity 262 may hold at least a portion of the dispensed medication for a period of time (e.g., 1 to 10 seconds, 1 to 30 seconds, 1 to 60 seconds, 1 to 2 minutes, 1 to 10 minutes, 1 to 30 minutes, 1 to 60 minutes, 1 to 120 minutes and/or other ranges therebetween). In other implementations, the interior cavity defines a channel through which the dispensed medication passes from the medication dispenser to the waste container 125, either directly, or indirectly through a portion of the locking mechanism 310.

The manifold assembly 260 may be positioned above the waste container 125 to allow the wasted medication to pass from the medication dispenser 290 to the waste container 125 or the interior cavity 262 more easily, such as via gravity, or by physical manipulation of the medication dispenser 290 (e.g., depression of a syringe, squeezing an IV bag, and/or the like). In some implementations, the manifold assembly 260 includes one or more valves to allow the medication to pass from the medication dispenser into the interior cavity, and/or from the interior cavity to the waste container 125. The one or more valves may be controlled by the controller 230. For example, the controller 230 may open and/or close the one or more valves depending on which medication dispenser 290 is dispensing the medication into the waste container 125. In some implementations, at least one of the valves, such as a flush valve, is coupled to a flush line. The flush line is configured to deliver a flushing solution to the manifold assembly 260 and/or to the flow path of the wasted medication to clean at least a portion of the flow path from the medication dispenser to the waste container 125. In some implementations, the controller 230 is configured to actuate the flush valve to allow the flushing solution to clean the flow path periodically, after a predetermined amount of medication has been wasted, after each medication dispenser 290 has been emptied, and/or at other designated time intervals. Flushing at least a portion of the flow path of the wasted medication helps to ensure that the flow path does not become clogged and/or that the one or more sensors are accurately measuring and/or identifying the wasted medication being deposited into the waste container 125. In some implementations, the one or more valves may allow at least some of the wasted medication to pass between the compartment 264 and the waste container 125.

The manifold assembly 260 may include a sequencing mechanism 266. The sequencing mechanism 266 causes the manifold assembly 260 to rotate and/or otherwise move into a proper position such that the desired medication dispenser 290, and/or compartment 264 is appropriately located along the flow path to the waste container 125. In some implementations, the controller 230 may cause the sequencing mechanism 266 to rotate the manifold assembly 260 in a sequence. For example, the sequencing mechanism 266 may rotate (e.g., automatically) the manifold assembly 260 to the next medication dispenser to dispense the wasted medication at set time intervals, after the current medication dispenser is emptied, and/or after a predetermined amount of medication has been deposited into the waste container 125. For example, because the medication analyzer 242 may take several seconds to identify the wasted medication, the sequencing mechanism 266 and/or the manifold assembly 260 allow for multiple medication dispensers 290 to be coupled to the wasting station 110, and allow for sequencing of the wasted medication to pass through the medication analyzer 242 from the manifold assembly 260 and/or the medication dispenser 290 after the medication analyzer 242 has identified the wasted medication from the corresponding medication dispenser. The sequencing mechanism 266 may rotate the manifold assembly 260 by 90 degrees, 180 degrees, 270 degrees, and/or the like. The sequencing mechanism helps to more efficiently and/or quickly dispense the medication into the waste container 125 with, or without, requiring a clinician to manipulate the medication dispenser.

Figure 7:
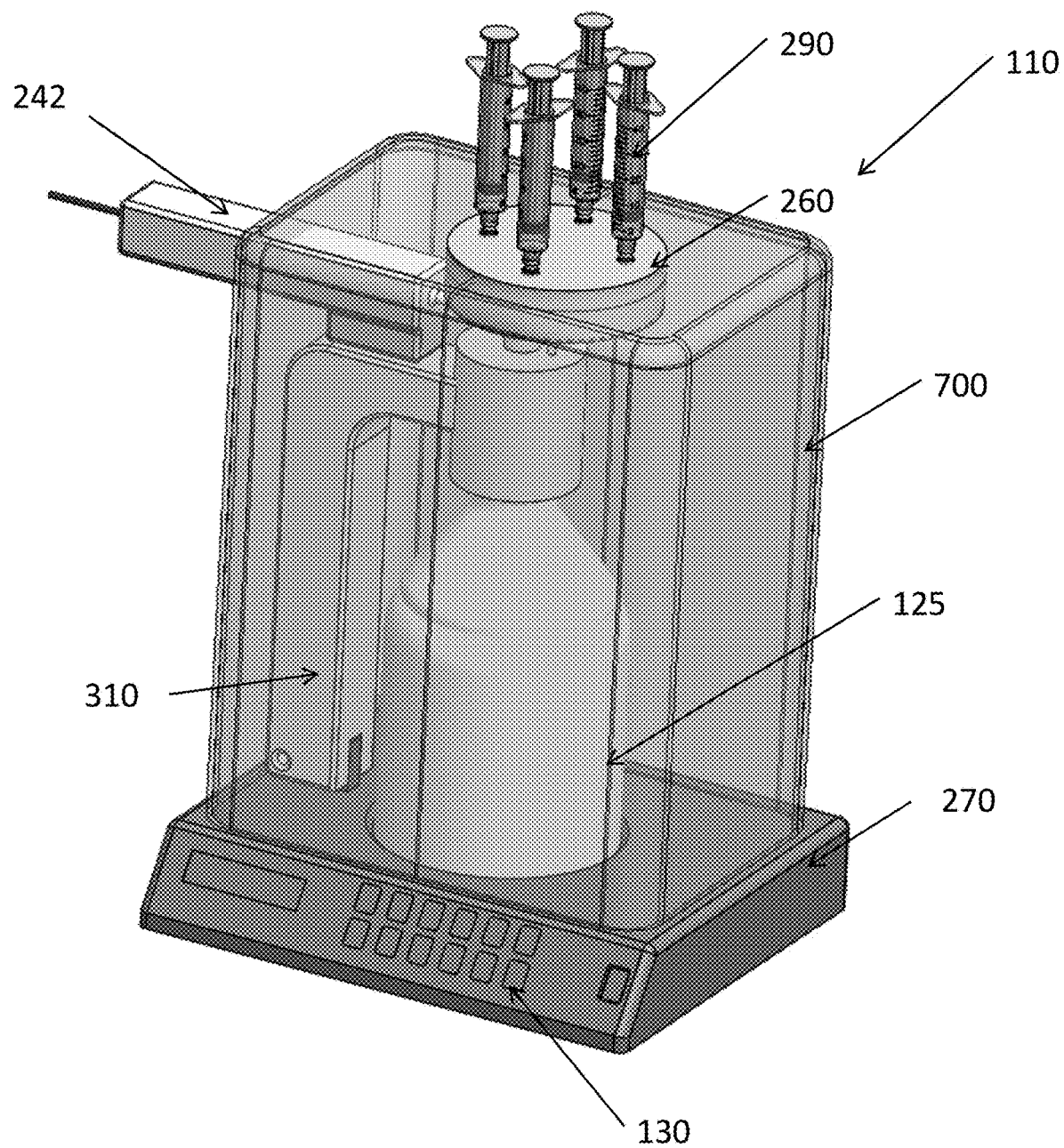
FIG. 7 depicts an example wasting station, consistent with implementations of the current subject matter.

FIG. 7 illustrates another example of the wasting station 110, consistent with implementations of the current subject matter, in which the wasting station 110 includes an enclosure 700. The enclosure 700 may be formed of plastic, metal, or another material to secure at least the waste container 125, the locking mechanism 310, the sensor 250B, the manifold assembly 260, and/or the medication dispenser 290. For example, as shown in FIG. 7, the enclosure 700 is supported by the base 270 and surrounds at least a portion of the waste container 125 and the locking mechanism 310 to prevent unauthorized access to the waste container 125 and its contents, thereby reducing or eliminating the risk of diversion of the wasted medication.

In some implementations, the enclosure 700 may be removably coupled to the wasting station 110, such as to the base 270. For example, after authorizing a user, such as via the user interface 130, the controller 230 may open at least a portion of the enclosure 700 to allow access to the waste container 125. In other implementations, after authorizing a user, such as via the user interface 130, the controller 230 may cause the enclosure 700 to unlock, thereby allowing for the enclosure to be removed, and/or to pivot along with the locking mechanism 310 when the locking mechanism 310 moves from the unlocked position to the unlocked positon. Thus, the enclosure 700 may provide enhanced security for the wasting station 110, as a second means (e.g., in addition to the locking mechanism 310) of preventing unauthorized access to the waste container 125. In some implementations, the enclosure 700 is not removable until the wasting station 110 grants access to the waste container 125 via a dual-authentication process. For example, the wasting station 110 may grant a first authorization to allow the locking mechanism 310 to be unlocked and a second authorization to allow the enclosure to be moved. Alternatively, the wasting station 110 may grant a first authorization to allow the enclosure to be moved and a second authorization for the locking mechanism 310 to be unlocked. The enclosure 700 may also shield at least a portion of the flow path between the medication dispenser 290 and the waste container 125, including the medication analyzer 242, from manipulation from an unauthorized user during the wasting process.

FIGS. 8-11 illustrate an example of a wasting station 810, consistent with implementations of the current subject matter. For example, the wasting station 810 illustrated in FIGS. 8-11 may include one or more of the same or similar properties and/or components of the wasting station 110, such as the base 270 (including one or more of the sensors 250 such as the weight sensor), the waste container 125, the locking system 300, the medication analyzer 242 including one or more sensors 250 such as the flow sensor and/or the optical sensor, and/or the manifold assembly 260. As shown, the wasting station 810 may additionally and/or alternatively include a sequencing mechanism 866, a plunger mechanism 868, and/or an enclosure 800.

The wasting station 810 may allow for the medication to be wasted from the medication dispenser 290 automatically, without intervention from a user during the wasting process. For example, as noted above, the wasting station 810 includes the sequencing mechanism 866 and the plunger mechanism 868. The sequencing mechanism 866 may be the same or similar to the sequencing mechanism 266, and may include one or more of the same features and/or function as the sequencing mechanism 266. The sequencing mechanism 866 and the plunger mechanism 868 may be supported by and/or form a part of the manifold assembly 260.

Figure 8:
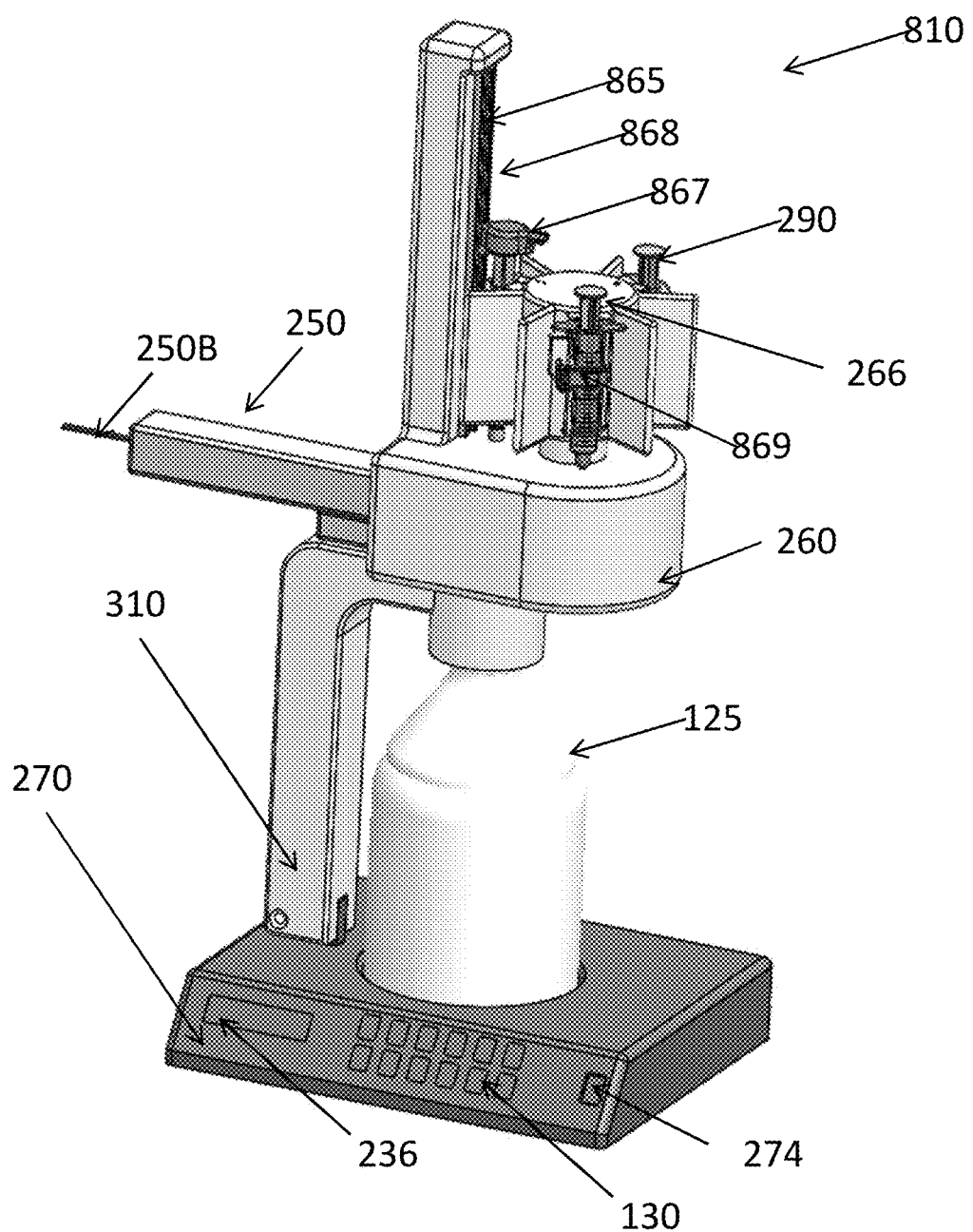
FIG. 8 depicts an example wasting station, consistent with implementations of the current subject matter.

The sequencing mechanism 866 positions the medication dispenser 290 to the plunger mechanism 868, which causes the medication dispenser 290 (e.g., by depressing, squeezing, and/or another type of physical manipulation) to dispense the wasted medication. For example, the sequencing mechanism 866 may extend from the manifold assembly 260. The sequencing mechanism may include structure shaped as a cylinder, rectangle, square, and/or the like. The sequencing mechanism 866 may include one or more attachment features 869 to secure at least one (one, two, three, four, five, six, seven, eight, or more medication dispensers) to the sequencing mechanism 866. The one or more attachment features 869 may include a clamp, magnet, snap-fit, or another attachment feature that secures the medication dispenser 290 to the sequencing mechanism 866. The one or more attachment features 869 may include one, two, three, four, five, six, seven, eight, or more attachment features 869, each of which configured to receive and secure at least a portion of a corresponding medication dispenser 290. As shown in FIG. 8, for example, the attachment feature 869 wraps around at least a portion of the medication dispenser 290 to secure the medication dispenser to the sequencing mechanism 866. The attachment feature 269 may hold the medication dispenser 290 in an upright position to allow for the medication dispenser 290 to more easily couple to the slot 261 when the medication dispenser 290 is located by the sequencing mechanism 866 within the plunger mechanism 868.

Figure 10:
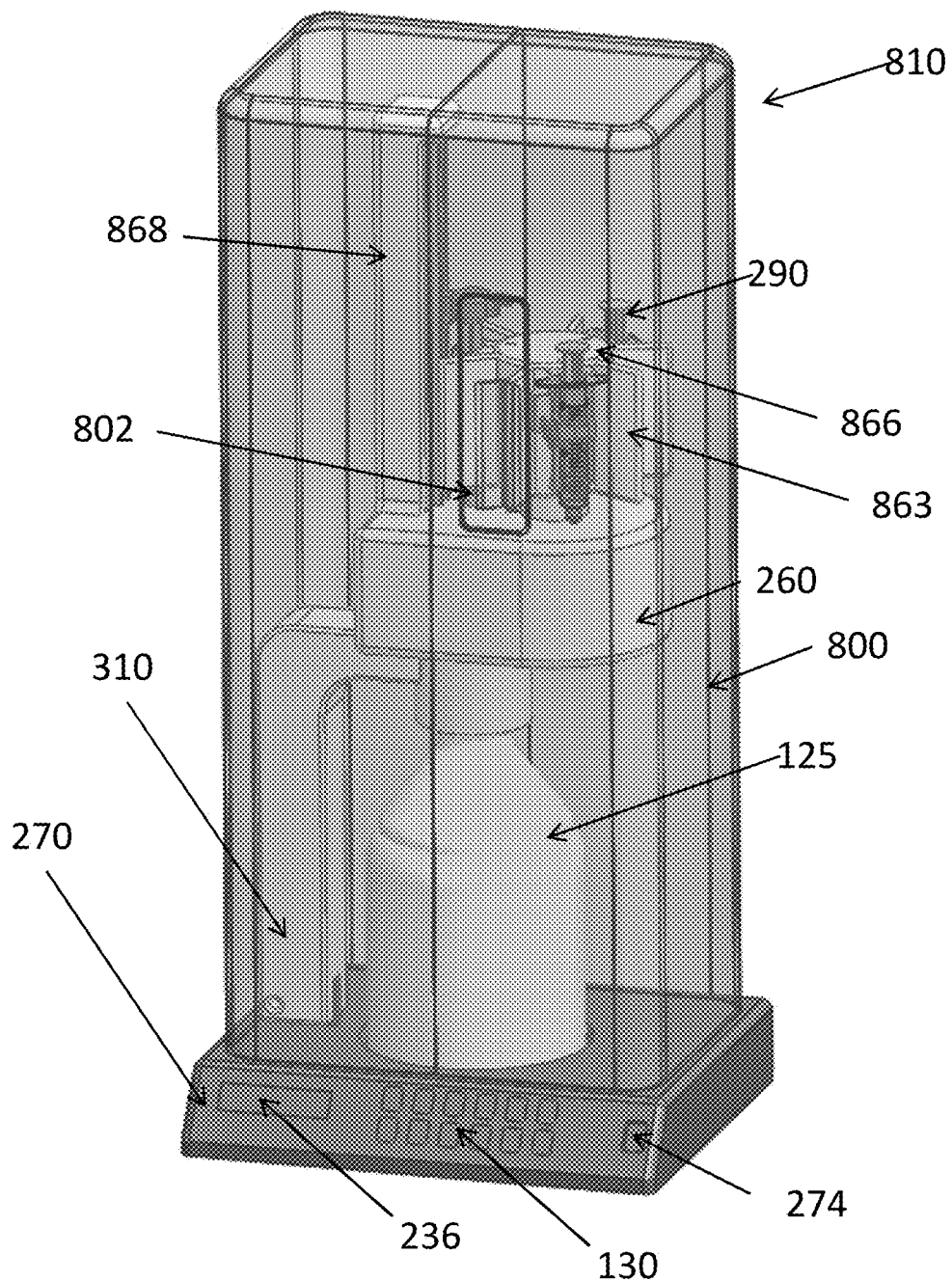
FIG. 10 depicts an example wasting station, consistent with implementations of the current subject matter.
Figure 11:
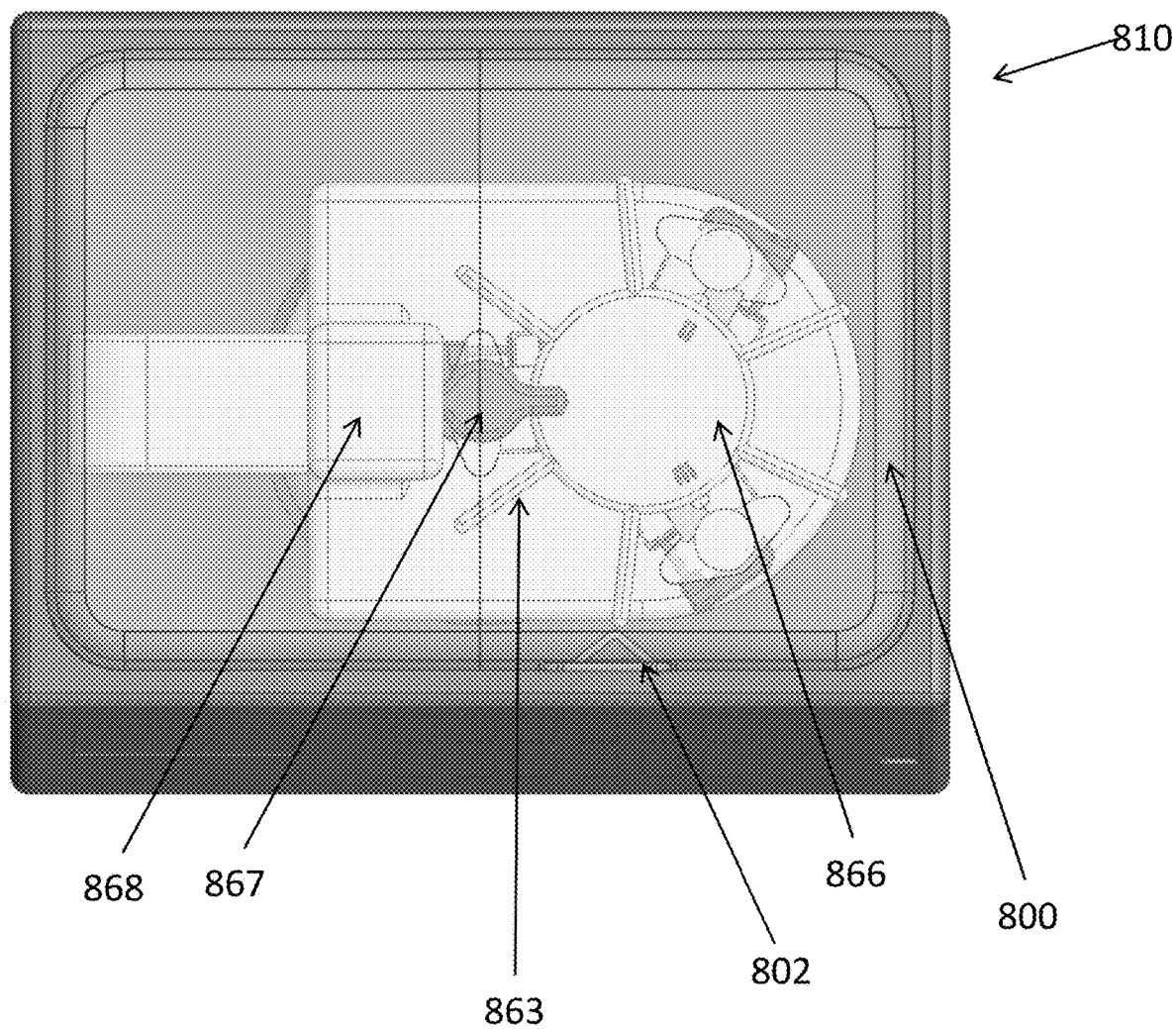
FIG. 11 depicts a top view of an example wasting station, consistent with implementations of the current subject matter.

The sequencing mechanism 866 may include one or more walls 863 that extend radially outwardly from a central portion of the sequencing mechanism 866 (see FIGS. 10-11). The one or more walls 863 are positioned between adjacent attachment features 869. In some implementations, the one or more walls 863 are configured to separate the medication dispensers when the medication dispensers are coupled to the wasting station 810.

The sequencing mechanism 866 rotates and/or otherwise moves into a proper position such that the desired medication dispenser 290 is appropriately within and/or coupled to the plunger mechanism 868. In some implementations, the controller 230 may cause the sequencing mechanism 866 to rotate the medication dispensers 290 in a sequence. For example, the sequencing mechanism 866 may rotate (e.g., automatically), after a first medication dispenser has dispensed the wasted medication, to a second, third, or fourth medication dispenser to dispense the wasted medication at set time intervals, after the first medication dispenser is emptied, and/or after a predetermined amount of medication has been deposited into the waste container 125. For example, because the medication analyzer 242 may take several seconds to identify the wasted medication, the sequencing mechanism 866 allows for multiple medication dispensers 290 to be coupled to the wasting station 110, and allows for sequencing of the wasted medication to pass to the waste container 125 after the medication analyzer 242 has identified the wasted medication from the corresponding medication dispenser. The sequencing mechanism 866 may rotate in sequence by 60 degrees, 90 degrees, 120 degrees, 180 degrees, 240 degrees, 270 degrees, 300 degrees, 330 degrees, 360 degrees, and/or the like, to position the next medication dispenser. The sequencing mechanism 866 helps to more efficiently and/or quickly dispense the medication into the waste container 125 without requiring a clinician to manipulate the medication dispenser.

Referring to FIGS. 8-12, the plunger mechanism 868 includes a dispensing feature 867 and a track 865. The dispensing feature 867 is configured to slide along the track 865. The dispensing feature 867 is configured to contact a portion of the medication dispenser 290 to cause at least some of the wasted medication to be dispensed from the medication dispenser. In the example illustrated in FIGS. 8-12, the dispensing feature 867 is configured to slide along the track 865 and contact and depress a plunger of the medication dispenser (e.g., a syringe in this scenario) to cause the wasted medication to be dispensed from the medication dispenser 290. The plunger mechanism 868 may include a motor or other power source, and/or may be coupled to an external power source. The controller 230 may activate the plunger mechanism 868 to cause the plunger mechanism 868 to contact the medication dispenser 290. For example, the controller 230 may send a command to the plunger mechanism 868 to cause the plunger mechanism to dispense at least some of the wasted medication from the medication dispenser 290. In some implementations, the plunger mechanism 868 causes the medication dispenser to dispense all of the wasted medication from the medication dispenser. In some implementations, the plunger mechanism 868 (e.g., after receiving a command from the controller 230) causes the medication dispenser to dispense a first portion of the wasted medication from the medication dispenser to be analyzed by the medication analyzer 242. In some implementations, the plunger mechanism (e.g., after receiving a command from the controller 230) causes the medication dispenser to dispense the remaining portion of the wasted medication from the medication dispenser after the medication analyzer 242 has identified the wasted medication.

Similar to the wasting station 110, the wasting station 810 may include one or more valves, such as a flush valve, that are coupled to a flush line. The flush line is configured to deliver a flushing solution through the slot 261 of the manifold assembly 260 and/or to the flow path of the wasted medication to clean at least a portion of the flow path from the medication dispenser to the waste container 125. In some implementations, the controller 230 is configured to actuate the flush valve to allow the flushing solution to clean the flow path periodically, after a predetermined amount of medication has been wasted, after each medication dispenser 290 has been emptied, and/or at other designated time intervals. Flushing at least a portion of the flow path of the wasted medication helps to ensure that the flow path does not become clogged and/or that the one or more sensors are accurately measuring and/or identifying the wasted medication being deposited into the waste container 125.

FIGS. 10 and 11 illustrate an example of the enclosure 800, which may be the same or similar to the enclosure 700, and may include one or more of the same features and/or function as the enclosure 700. The enclosure 800 may be formed of plastic, metal, or another material. The enclosure 800 may be supported by the base 270, and may secure at least a portion of the wasting station 810, such as the waste container 125, the locking mechanism 310, the sensor 250B, the manifold assembly 260, the sequencing mechanism 866, the plunger mechanism 868, and/or the medication dispensers 290 coupled to the wasting station 810. For example, as shown in FIGS. 10-11, the enclosure 800 is supported by the base 270 and surrounds the remaining components of the wasting station 810 to prevent unauthorized access to the waste container 125 and its contents and/or the medication dispensers coupled to the wasting station 810, thereby reducing or eliminating the risk of diversion of the wasted medication during the wasting process.

In some implementations, the enclosure 800 may be removably coupled to the wasting station 810, such as to the base 270. In some implementations, after authorizing a user, such as via the user interface 130, the controller 230 may open at least a portion of the enclosure 800 to allow access to the waste container 125, at least one medication dispenser 290, and/or the like. For example, the enclosure 800 may include an access door 802. The controller 230 may open the access door 802 to allow access to the waste container 125, at least one medication dispenser 290, and/or the like. As shown in FIGS. 10-11, the access door 802 provides access to at least one of the medication dispensers 290 coupled to the sequencing mechanism 866 for removal of the medication dispenser 290. Additionally and/or alternatively, the access door 802 provides access to at least one open position on the sequencing mechanism 866 at which no medication dispenser 290 is coupled to the sequencing mechanism 866.

The sequencing mechanism 866 may be capable of receiving a new medication dispenser at the open position. In some implementations, the access door 802 provides access to an open position on the sequencing mechanism 866 between two adjacent walls 863. Once the medication dispenser 290 is coupled to the sequencing mechanism 866, the sequencing mechanism 866 moves the medication dispenser away from the access door 802. The walls 863 and the access door 802, together with attachment features 869 may help to prevent or reduce the likelihood of unauthorized removal of the medication dispenser. This helps to ensure that only empty medication dispensers can be removed by an authorized user. As described herein, the enclosure 800 may only be opened by authorized user for removal of an empty medication dispenser, loading of a medication dispenser to the wasting station 810, and/or removal of the waste container 125.

In some implementations, after the controller 230 authorizes a user, such as via the user interface 130, the controller 230 may cause the enclosure 800 to unlock, thereby allowing for the enclosure to be removed, and/or to pivot along with the locking mechanism 310 when the locking mechanism 310 moves from the unlocked position to the unlocked positon. Thus, the enclosure 800 may provide enhanced security for the wasting station 810, as a second means (e.g., in addition to the locking mechanism 310) of preventing unauthorized access to the waste container 125.

Figure 12:
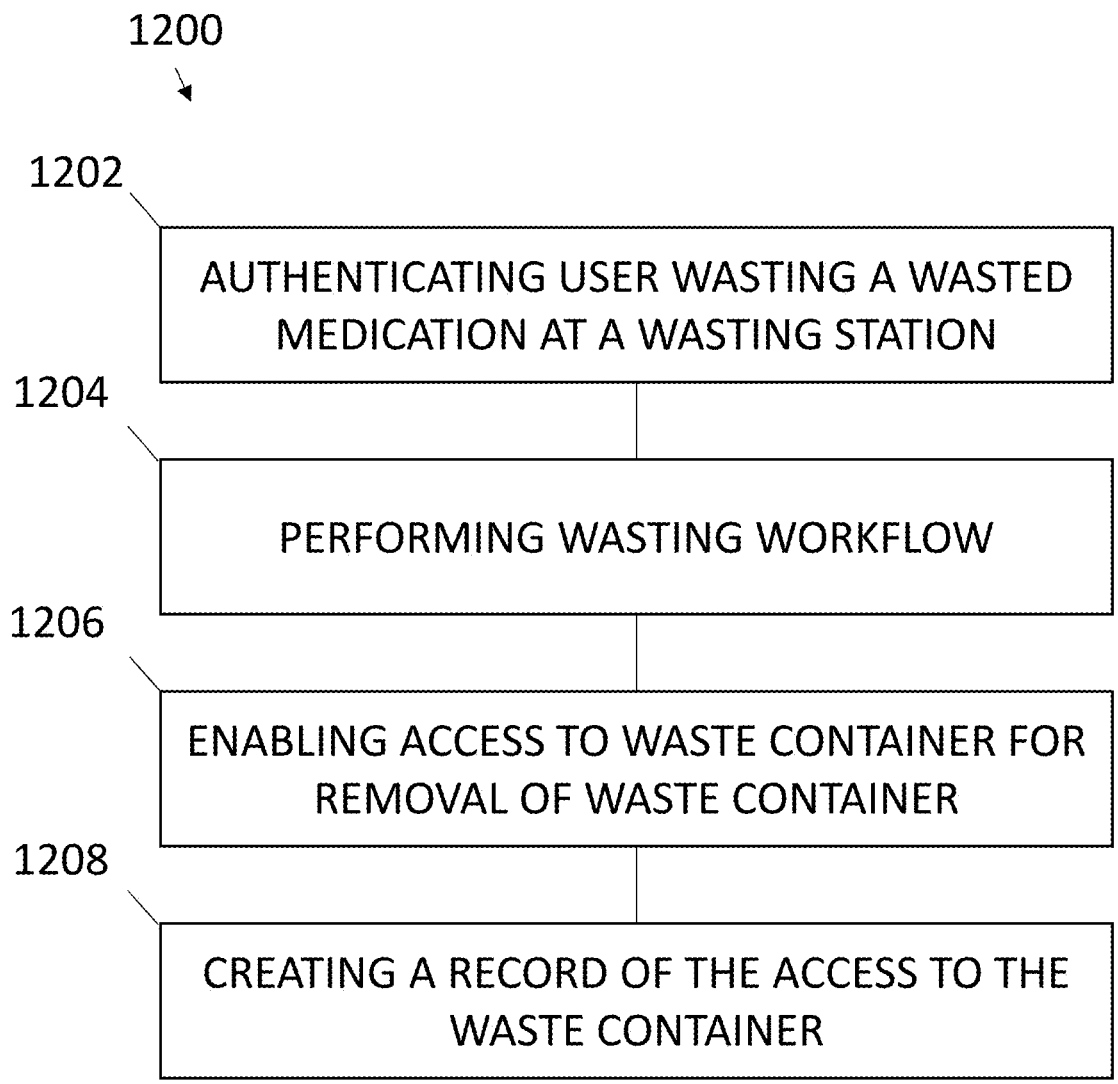
FIG. 12 is a flowchart illustrating a process, consistent with implementations of the current subject matter.

FIG. 12 depicts a flowchart illustrating an example process 1200, consistent with implementations of the current subject matter.

At 1202, a wasting station (e.g., the wasting station 110, 810), via a controller (e.g., the controller 230), may authenticate a user, such as the clinician 135, using the wasting station. The wasting station may receive one or more credentials from the user, such as via a user interface (e.g., the user interface 130). The user, via the user interface, may be prompted to enter a user name and password, provide a fingerprint scan, provide a retina scan, swipe an employee card, or provide other information, such as biometric information, to verify the user is authorized to use the wasting station 110.

At 1204, the wasting station may perform a wasting workflow. During and/or after authorization of the user, the wasting station may receive, via the user interface, a type of medication to be wasted and a quantity of medication to be wasted. In some implementations, the wasting station may receive an indication, such as via the user interface, that the wasting workflow should begin.

In some implementations, the wasting station may receive one or more medication dispensers. In other words, the user may couple one or more medication dispensers to the wasting station. For example, a manifold assembly (e.g., the manifold assembly 260) and/or a sequencing mechanism (e.g., the sequencing mechanism 266, 866) may receive one or more medication dispensers. In some implementations, one or more slots (e.g., the slots 261) on the manifold assembly may receive at least a portion of the medication dispenser. In such implementations, the user may position the medication dispenser such that an end of the medication that dispenses the wasted medication is coupled to a corresponding slot.

Additionally, and/or alternatively, the sequencing mechanism may receive at least a portion of the medication dispenser. In such implementations, the user may couple the medication dispenser to one or more attachment features on the sequencing mechanism. In some implementations, the wasting station includes an enclosure that surrounds at least the sequencing mechanism. After the wasting station authorizes the user, the controller of the wasting station may cause an access door in the enclosure to open, allowing access to at least one of the attachment features for the user to load the medication dispenser onto the wasting station.

In some implementations, as part of the wasting workflow, the controller causes rotation of the medication dispenser, such as via the sequencing mechanism. For example, the medication dispenser is rotated by the wasting station to position the medication dispenser to dispense the wasted medication along a flow path (e.g., through the manifold assembly and/or medical analyzer) to a waste container coupled to the wasting station. Once the medication dispenser is in the proper position, the at least a portion of the wasted medication may be dispensed. In some implementations, the user may physically manipulate the medication dispenser to dispense the medication. Additionally and/or alternatively, rotation of the medication dispenser causes the medication dispenser to couple with a plunger mechanism. The plunger mechanism may contact the medication dispenser to cause the wasted medication to be dispensed. As described herein, such configurations may provide an automated process that efficiently wastes medication. This may also allow for a closed system that causes the wasted medication to be dispensed into the waste container while preventing unauthorized access to the wasted medication and/or the waste container.

In some implementations, the wasting station may include one or more valves, such as a flush valve, that are coupled to a flush line. The flush line is configured to deliver a flushing solution through at least a portion of the flow path clean at least the portion of the flow path. In some implementations, the controller is configured to actuate the flush valve to allow the flushing solution to clean the flow path periodically, after a predetermined amount of medication has been wasted, after each medication dispenser has been emptied, and/or at other designated time intervals. Flushing at least a portion of the flow path of the wasted medication helps to ensure that the flow path does not become clogged and/or that the one or more sensors accurately measure and/or identify the wasted medication being deposited into the waste container.

Figure 13:
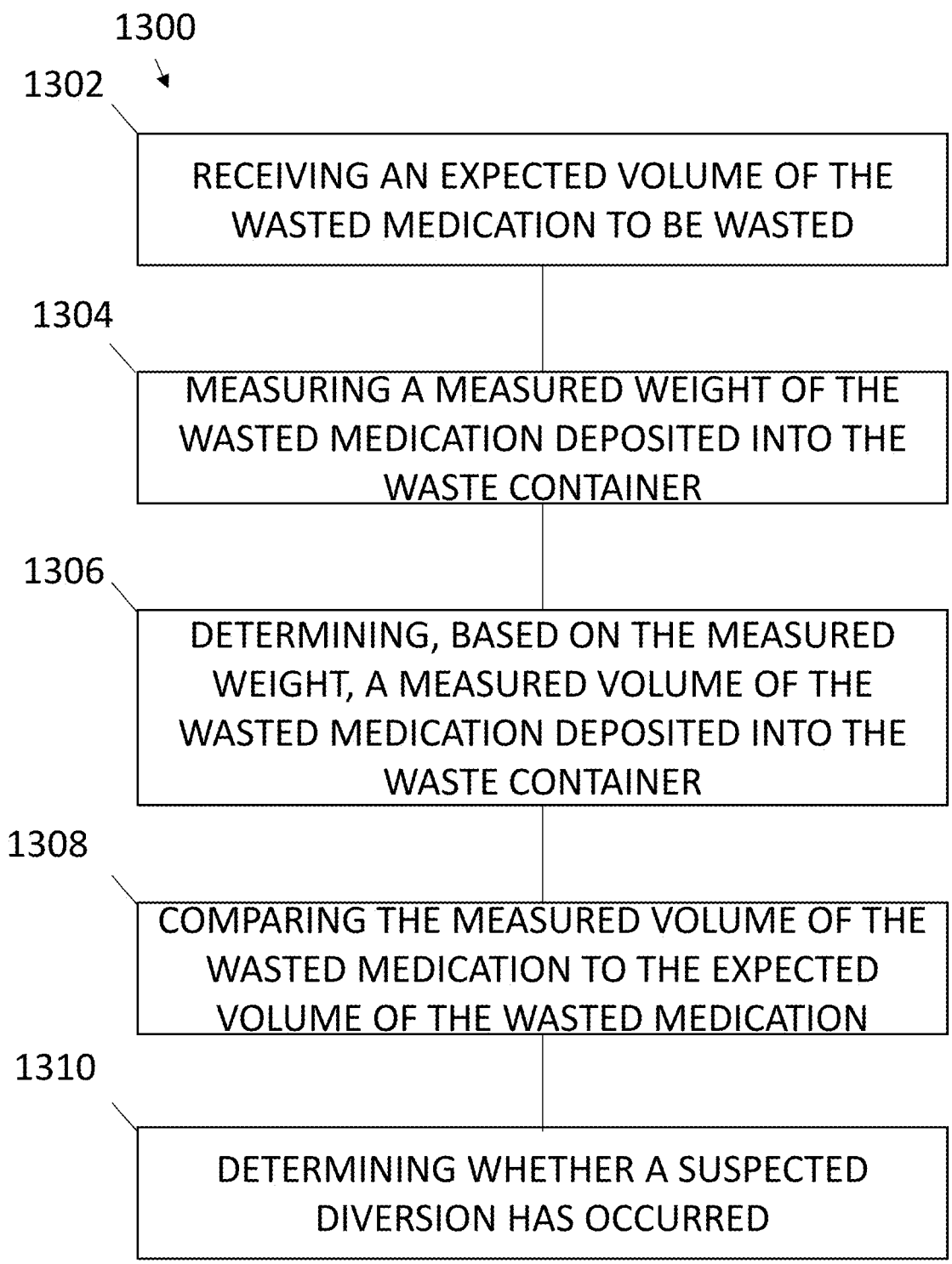
FIG. 13 is a flowchart illustrating an example wasting workflow, consistent with implementations of the current subject matter.

Before, during, and/or after the wasted medication is dispensed, the wasting station may perform one or more wasting workflows to help limit or prevent diversion of the wasted medication. FIG. 13 depicts an example wasting workflow 1300, consistent with implementations of the current subject matter. At 1302, as noted above, the wasting station may receive, via the user interface, an expected volume of the wasted medication to be wasted.

At 1304, the one or more weight sensors described herein may measure a measured weight of the wasted medication deposited into the waste container. For example, as described herein, the base of the wasting station may include a weight sensor positioned beneath the waste container. The weight sensor may measure a weight of the waste container, including its contents. The weight sensor may determine the measured weight of the wasted medication deposited into the waste container by subtracting a weight of the waste container.

At 1306, based on the measured weight, the wasting station (e.g., the controller) may determine a measured volume of the wasted medication deposited into the waste container. For example, the controller may convert the measured weight of the wasted medication to the measured volume of the wasted medication. In some implementations, the controller converts the measured weight of the wasted medication to the measured volume of the wasted medication based on a density of the wasted medication. The controller may retrieve the density of the wasted medication from a database of the wasting station and/or communicatively coupled to the wasting station. In other implementations, the wasting station receives the density of the wasted medication via the user interface.

At 1308, the wasting station (e.g., the controller) compares the measured volume of the wasted medication to the expected volume of the wasted medication. For example, the wasting station may determine whether the measured volume is the same as or within an acceptable range of the expected volume.

At 1310, the wasting station (e.g., the controller) may determine whether a suspected diversion has occurred. For example, the wasting station may determine that a suspected diversion of the wasted medication has occurred based upon a determination that the measured volume is not the same as or is not within an acceptable range of the expected volume. Based on the determination of the suspected diversion, the wasting station may store information associated with the user, either collected during authorization of the user or from a database, and information associated with the wasted medication, such as the expected volume, the measured volume, and/or the like, for later audit. In some implementations, based on the determination of the suspected diversion, the wasting station generates an alert, flags the wasting workflow for later audit, generates an alert at a remote location, and/or the like. Additionally and/or alternatively, the wasting station may determine that a suspected diversion of the wasted medication has not occurred based upon a determination that the measured volume is the same as or is within an acceptable range of the expected volume. Based on the determination that no suspected diversion has occurred, the wasting station may store information associated with the user, either collected during authorization of the user or from a database, and information associated with the wasted medication, such as the expected volume, the measured volume, and/or the like, for later audit.

Figure 14:
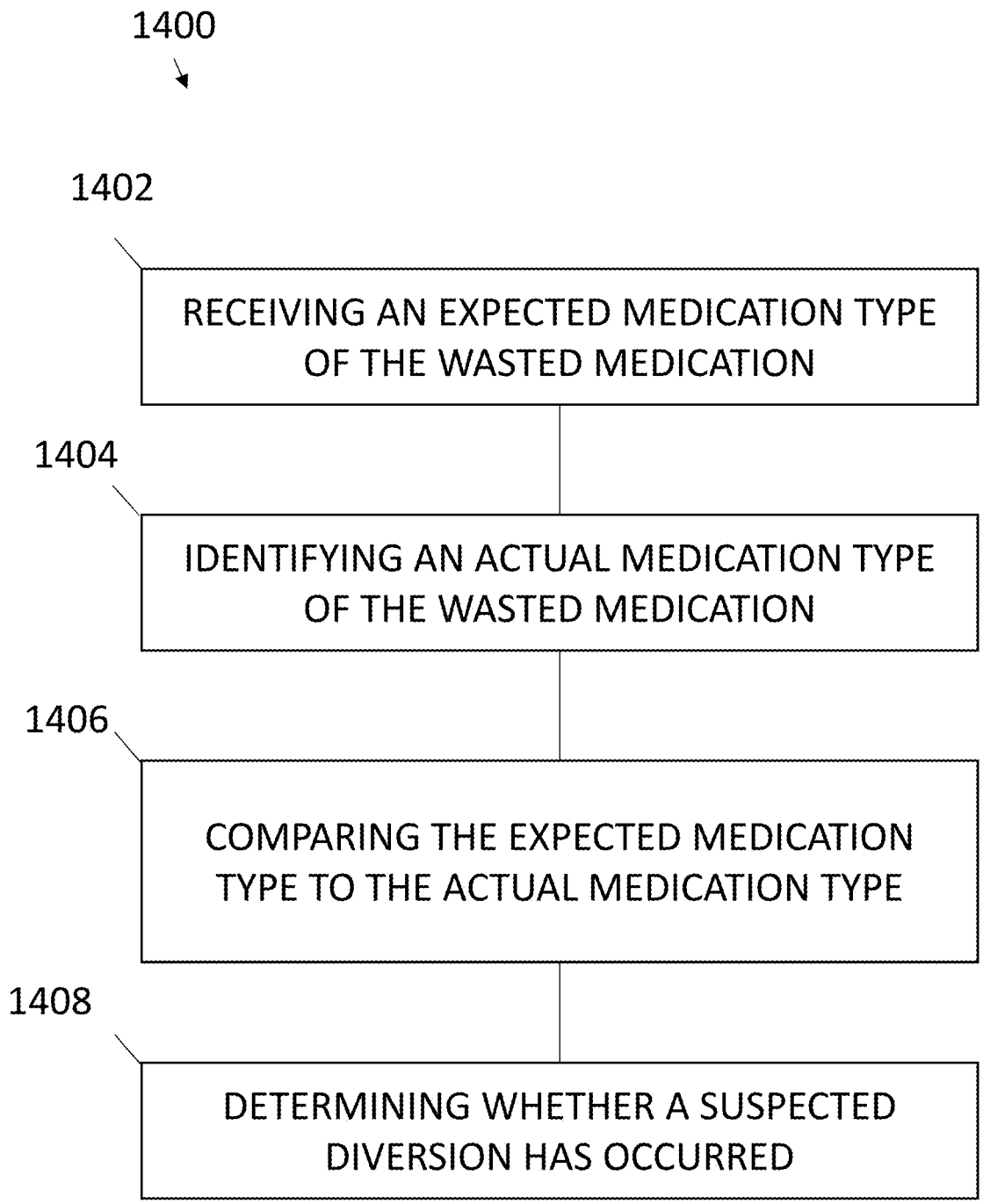
FIG. 14 is a flowchart illustrating an example wasting workflow, consistent with implementations of the current subject matter.
Figure 15:
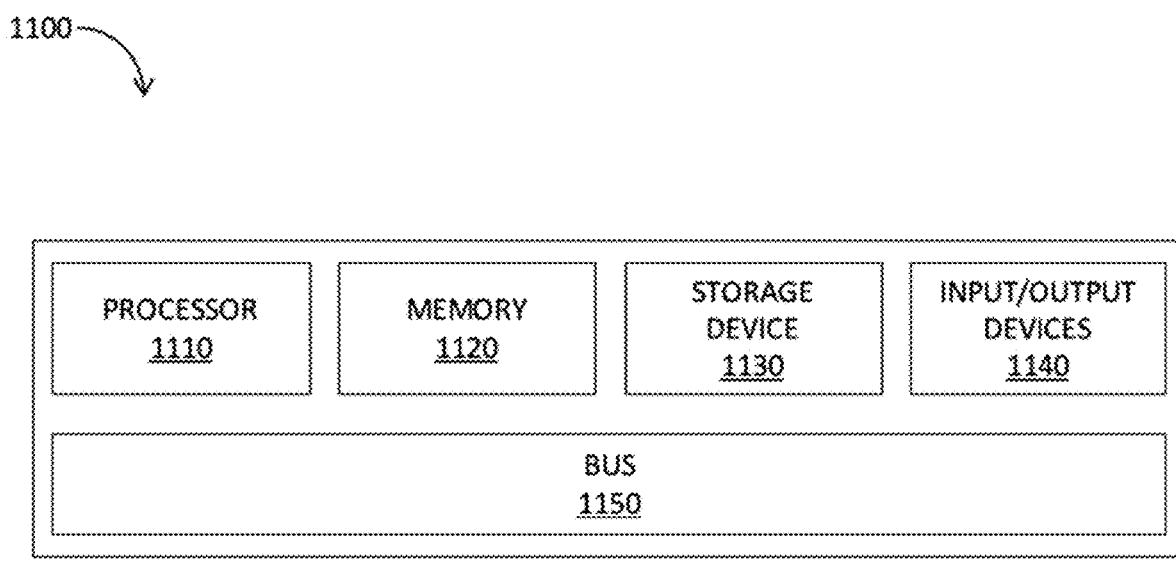
FIG. 15 depicts a block diagram illustrating a computing system consistent with implementations of the current subject matter.

FIG. 14 depicts another example wasting workflow 1400, consistent with implementations of the current subject matter. At 1402, as noted above, the wasting station may receive, via the user interface, an expected medication type of the wasted medication to be wasted.

At 1404, the medication analyzer (e.g., the medication analyzer 242) including one or more sensors, such as the optical sensor, described herein may identify an actual medication type of the wasted medication deposited into the waste container. For example, the medication analyzer may identify the medication type of the wasted medication as the wasted medication passes along the flow path. Additionally and/or alternatively, the medication analyzer collects a portion of the wasted medication to analyze.

At 1406, the wasting station (e.g., the controller) compares the expected medication type to the actual medication type of the wasted medication. For example, the wasting station may determine whether the identified actual medication type is the same as the expected medication type.

At 1408, the wasting station (e.g., the controller) may determine whether a suspected diversion has occurred. For example, the wasting station may determine that a suspected diversion of the wasted medication has occurred based upon a determination that the actual medication type is not the same as the expected medication type. Based on the determination of the suspected diversion, the wasting station may store information associated with the user, either collected during authorization of the user or from a database, and information associated with the wasted medication, such as the expected medication type, the actual medication type, and/or the like, for later audit. In some implementations, based on the determination of the suspected diversion, the wasting station generates an alert, flags the wasting workflow for later audit, generates an alert at a remote location, and/or the like. Additionally and/or alternatively, the wasting station may determine that a suspected diversion of the wasted medication has not occurred based upon a determination that the actual medication type is the same as the expected medication type. Based on the determination that no suspected diversion has occurred, the wasting station may store information associated with the user, either collected during authorization of the user or from a database, and information associated with the wasted medication, such as the expected medication type, the actual medication type, and/or the like, for later audit.

Referring back to FIG. 12, at 1206, the wasting station may enable access to the waste container for removal of the waste container. In some implementations, the wasting station determines that the waste container is ready for removal, such as when the waste container has reached its maximum storage capacity and/or after a medication dispenser has been emptied. Additionally and/or alternatively, the wasting station may receive a request to access and/or remove the waste container.

Based on the determination that the waste container is ready for removal and/or the receipt of the request to access and/or remove the waste container, the wasting station may authenticate the user. The wasting station may receive one or more credentials from the user, such as via the user interface, which may be associated with the wasted medication, the removal and/or access of the waste container, and/or the like, and stored for later audit. The user, via the user interface, may be prompted to enter a user name and password, provide a fingerprint scan, provide a retina scan, swipe an employee card, or provide other information, such as biometric information, to verify the user is authorized to use the wasting station.

To enable access to the waste container for removal of the waste container, the wasting station may unlock an enclosure surrounding at least a portion of the wasting station. Additionally and/or alternatively, to enable access to the waste container for removal of the waste container, the wasting station may cause a locking mechanism securing the waste container to the wasting station to unlock. Unlocking the locking mechanism may include pivoting the locking mechanism from a first position, in which a portion of the locking mechanism is positioned over an open end of the waste container, to a second positon, in which the portion of the locking mechanism is positioned away from the open end of the waste container, and allows access to the waste container.

At 1208, the wasting station may create a record of the access to the waste container. For example, as noted above, the wasting station may associate one or more of the credentials of the user with one or more details about the wasted medication. The wasting station may store the association between the user and the wasted medication and/or the waste container for later audit.

Accordingly, the wasting station described herein may accurately measure and/or track the dispensed weight and/or volume of the wasted medication that is deposited into and/or captured by the waste container. The wasting system may additionally and/or alternatively identify the wasted medication, such as when the medication is deposited into the waste container. This helps to limit or prevent diversion of the wasted medication, by creating records of the wasting process for later audit, and by providing a system that flags a particular wasting process for later audit at least when the system determines that a suspected diversion has occurred. The wasting system may additionally and/or alternatively secure the wasting station, such that only authorized users may access one or more components of the wasting station, further preventing or limiting diversion of the wasted medication. Additionally and/or alternatively, the wasting station described herein may reduce the resources required to waste medication and allows users to perform additional tasks while the wasting station performs the wasting process. This may also improve the user experience of the wasting system while wasting medication.

FIG. 11 depicts a block diagram illustrating a computing system 1100 consistent with implementations of the current subject matter. Referring to FIG. 1A, FIG. 1B, and FIG. 2, the computing system 1100 may be used to implement one or more components of the wasting system 100, such as the various components of the wasting station 110.

As shown in FIG. 11, the computing system 1100 may include a processor 1110, a memory 1120, a storage device 1130, and input/output device 1140. The processor 1110, the memory 1120, the storage device 1130, and the input/output device 1140 may be interconnected via a system bus 1150. The processor 1110 is capable of processing instructions for execution within the computing system 1100. Such executed instructions may implement one or more components of the wasting system 100, such as the wasting station 110. In some example embodiments, the processor 1110 may be a single-threaded processor. Alternatively, the processor 1110 may be a multi-threaded processor. The processor 1110 is capable of processing instructions stored in the memory 1120 and/or on the storage device 1130 to display graphical information for a user interface provided via the input/output device 1140.

The memory 1120 is a computer readable medium such as volatile or non-volatile that stores information within the computing system 1100. The memory 1120 may store data structures representing configuration object databases, for example. The storage device 1130 is capable of providing persistent storage for the computing system 1100. The storage device 1130 may be a floppy disk device, a hard disk device, an optical disk device, a tape device, a solid-state device, and/or any other suitable persistent storage means. The input/output device 1140 provides input/output operations for the computing system 1100. In some implementations, the input/output device 1140 includes a keyboard and/or pointing device. In various implementations, the input/output device 1140 includes a display unit for displaying graphical user interfaces.

According to some implementations, the input/output device 1140 may provide input/output operations for a network device. For example, the input/output device 1140 may include Ethernet ports or other networking ports to communicate with one or more wired and/or wireless networks (e.g., a local area network (LAN), a wide area network (WAN), the Internet).

In some implementations, the computing system 1100 may be used to execute various interactive computer software applications that may be used for organization, analysis, and/or storage of data in various formats. Alternatively, the computing system 1100 may be used to execute any type of software applications. These applications may be used to perform various functionalities, e.g., planning functionalities (e.g., generating, managing, editing of spreadsheet documents, word processing documents, and/or any other objects, etc.), computing functionalities, communications functionalities, etc. The applications may include various add-in functionalities or may be standalone computing products and/or functionalities. Upon activation within the applications, the functionalities may be used to generate the user interface provided via the input/output device 1140. The user interface may be generated and presented to a user by the computing system 1100 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and one or more hardware buttons, a keyboard and/or a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices, hardware buttons, and associated interpretation software, and the like.

Although the disclosure, including the figures, described herein may describe and/or exemplify different variations separately, it should be understood that all or some, or components of them, may be combined.

Although various illustrative embodiments are described above, any of a number of changes may be made to various embodiments. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. References to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as, for example, "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

Throughout this specification and the claims which follow, unless the context requires otherwise, the word "comprise" and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" "or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, are possible.

In the descriptions above and in the claims, phrases such as, for example, "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wasting station configured to receive a wasted medication from a medication dispenser, comprising:
 a base comprising:
  a substantially horizontal surface configured to support a waste container in an upright position such that a closed portion of the waster container is on the surface;
  a weight sensor configured to measure a weight of a waste container supported by the base, the wasting station configured to determine, based on the measured weight, a volume of the wasted medication positioned within the waste container; and a locking mechanism comprising:
- a first end configured to be coupled to the base; and
- a second end configured to be coupled to the waste container when the locking mechanism is in a first position and decoupled from the waste container when the locking mechanism moves from the first position to a second position, thereby allowing for removal of the waste container, wherein the second end directly attaches an open end of the waste container when the locking mechanism is in the first position to prevent removal of the waste container.

2. The wasting station of claim 1, further comprising:
a manifold assembly configured to receive the medication dispenser, the manifold assembly comprising an interior cavity configured to receive at least a portion of the wasted medication from the medication dispenser.

3. The wasting station of claim 2, wherein the manifold assembly comprises a sequencing mechanism, the sequencing mechanism configured to rotate the manifold assembly to allow for a second medication dispenser to dispense the wasted medication into the interior cavity.

4. The wasting station of claim 2, wherein the manifold assembly (Original) comprises a valve configured to allow the wasted medication to pass between the interior cavity and the waste container.

5. The wasting station of claim 2, wherein the manifold assembly comprises a valve configured to allow the wasted medication to pass between the medication dispenser and the interior cavity.

6. The wasting station of claim 1, further comprising a medication analyzer positioned along a flow path between the manifold assembly and the waste container, the medication analyzer comprising a sensor to measure one or more aspects of the wasted medication.

7. The wasting station of claim 6, wherein the sensor comprises one or more of: a flow sensor and an optical sensor; wherein the flow sensor is configured to determine the volume of the wasted medication; and wherein the optical sensor is configured to identify a type of the wasted medication.

8. The wasting station of claim 1, wherein the base comprises a recess, the recess configured to secure the closed portion of the waste container; and wherein the locking mechanism is configured to secure the opened portion of the waste container, the opened portion opposite the closed portion, the opened portion configured to receive the wasted medication.

9. The wasting station of claim 8, wherein the recess comprises the weight sensor.

10. The wasting station of claim 1, wherein the base further comprises a user interface configured to receive one or more inputs by a user, the input comprising an expected volume of the wasted medication.

11. The wasting station of claim 1, further comprising an enclosure configured to surround at least at least the waste container and at least a portion of the locking mechanism.

12. The wasting station of claim 1, further comprising a plunger mechanism configured to depress the medication dispenser to cause the wasted medication to be displaced from the medication dispenser.

13. The wasting station of claim 12, further comprising a sequencing mechanism, the sequencing mechanism configured to retain and position the medication dispenser in contact with the plunger mechanism, thereby allowing the plunger mechanism to depress the medication dispenser.

14. The wasting station of claim 13, wherein the sequencing mechanism is configured to rotate medication dispenser into contact with the plunger mechanism.

15. The wasting station of claim 11, wherein the enclosure comprises an access door, the access door configured to one or more of: allow access to the medication dispenser, allow the medication dispenser to be removed, and allow the medication dispenser to be coupled to the wasting station.

16. The wasting station of claim 1, further comprising:
- a controller; and
- at least one memory storing instructions.

17. The wasting station of claim 16, wherein the at least one memory storing instructions, which, when executed by the controller, result in operations comprising:
- authenticating the user;
- performing a wasting workflow;
- enabling access to the waste container for removal of the waste container; and
- creating a record of the access to the waste container.

18. The wasting station of claim 17, wherein the enabling access further comprises: causing the locking mechanism to move from the first position to the section position.

19. A system, comprising:
- a wasting station, comprising:
  - a base comprising a weight sensor configured to measure a weight of a waste container supported by the base and a substantially horizontal surface configured to support the waste container in an upright position such that a closed portion of the waster container is on the surface,
  - a locking mechanism coupled to the base and configured to secure the waste container to the base, the locking mechanism comprising a first end coupled to the base and a second end coupled to the waste container when the locking mechanism is in a first position and decoupled from the waste container when the locking mechanism moves from the first position to a second position, thereby allowing for removal of the waste container, wherein the second end directly attaches an open end of the waste container when the locking mechanism is in the first position to prevent removal of the waste container;
- at least one data processor associated with the wasting station; and
- at least one memory storing instructions which, when executed by the at least one data processor, result in operations comprising:
  - authenticating a user;
  - performing a wasting workflow, the wasting workflow comprising depositing a wasted medication into the waste container;
  - enabling access to the waste container for removal of the waste container; and
  - creating a record of the access to the waste container.

* * * * *